(12) United States Patent
Shimura et al.

(10) Patent No.: US 6,899,678 B2
(45) Date of Patent: May 31, 2005

(54) PUNCTURE DIFFICULTY EVALUATING DEVICE

(75) Inventors: Takaki Shimura, Hiratsuka (JP); Yasuharu Nimura, Osaka (JP); Wataru Yoshioka, Osaka (JP)

(73) Assignees: Tokai University Educational System, Tokyo (JP); Medico's Hirata Inc., Osaka (JP)

( * ) Notice: Subject to any disclaimer, the term of this patent is extended or adjusted under 35 U.S.C. 154(b) by 0 days.

(21) Appl. No.: 10/689,761

(22) Filed: Oct. 22, 2003

(65) Prior Publication Data

US 2004/0087855 A1 May 6, 2004

(30) Foreign Application Priority Data

Oct. 23, 2002 (JP) ........................................ 2002-308777

(51) Int. Cl.[7] ................................................ A61B 8/12
(52) U.S. Cl. ..................................... 600/437; 600/461
(58) Field of Search ............................... 600/437–438, 600/443, 447, 454–456, 461

(56) References Cited

U.S. PATENT DOCUMENTS

| | | | |
|---|---|---|---|
| 3,936,791 A | | 2/1976 | Kossoff |
| 4,442,844 A | | 4/1984 | Navach |
| 5,038,787 A | * | 8/1991 | Antich et al. ............... 600/437 |
| 5,131,394 A | * | 7/1992 | Gehlbach .................... 600/461 |
| 5,235,987 A | | 8/1993 | Wolfe |
| 5,268,876 A | * | 12/1993 | Rachlin ......................... 367/7 |
| 5,402,681 A | * | 4/1995 | Nakaso et al. ................ 73/602 |
| 6,682,483 B1 | * | 1/2004 | Abend et al. ............... 600/437 |

FOREIGN PATENT DOCUMENTS

| | | |
|---|---|---|
| EP | 0 383 288 A1 | 8/1990 |
| JP | 5-168636 A | 7/1993 |
| JP | 7-184998 A | 7/1995 |
| JP | 11-151244 A | 6/1999 |

OTHER PUBLICATIONS

Hasegawa M., et al., "Diagnosis of Carotid Arterial Lesions and its Clinical Application—With Special Reference to Cerebral Circulation", vol. 35, No. 6, p349–358, 1995.
Yamazaki Y., et al., Detection of Early Change in Carotid Arteriosclerosis by Ultrasound high–resolution B–made imaging, Diabetes Journal, vol. 23, No. 1, pp 25–27, 1990.
Handa N., et al., Ultrasonic Evaluation of Early Carotid Atherosclerosis, Stroke, vol. 21, No. 11, pp1567–1572, 1990.
J. G. Miller, et al., "Myocardial Tissue Characterization: An Approach Based On Quantitative Backscatter And Attenuation", IEEE, Ultrasonic Symposuim pp782–793, 1983.
Philips Medical Systems: "User's Guide. Philips Sonos 5500/4500", Jun. 2002, Philips Electronics U.S.A. XP002268606.
Bridal et al.: "Relationship Between Ultrasonic Attenuation, Apparent Integrated Backscatter (30 To 50 MHZ) and the Composition of Atherosclerotic Plaque" Acoustical Imaging, vol. 23, Apr. 13–16, 1997, pp. 181–186, XP001172969.

* cited by examiner

*Primary Examiner*—Francis J. Jaworski
(74) *Attorney, Agent, or Firm*—Sughrue Mion, PLLC

(57) ABSTRACT

The present invention aims to provide a puncture difficulty evaluating device which can readily evaluate the difficulty of puncture in a measuring point. To this end, a puncture difficulty device receives the ultrasound backscattered at the measurement point, determines an integral of the power of the ultrasound over a predetermined angle range, and generates a parameter indicating the difficulty of puncture in the measurement point based on the determined integral.

17 Claims, 23 Drawing Sheets

Fig. 6

PUNCTURE DIFFICULTY EVALUATING DEVICE

BACKGROUND OF THE INVENTION

1. Field of the Invention

The present invention relates to a puncture difficulty evaluating device (a device to evaluate difficulty in puncture) which, when making an injection or the like in an arm of a patient, for example, evaluates the difficulty of puncture for a site in the arm to be punctured with the injection needle.

2. Description of the Related Art

In recent years, with the medical progress, the changes of the medical environment or the like, intravascular injections including intravenous injection and intraarterial injection have been increasingly used both for patients in a serious or emergency condition and patients in a chronically debilitated condition. The primary reasons for this are as follows.

(1) Many drugs are much more effective in the case of intravascular injection or continuous intravenous drip infusion than in the case of oral administration (impossible for patients in a serious condition) or subcutaneous injection. For example, this holds true for administration of cardiotonic drugs, hypertensive drugs, antihypertensive drugs, anticoagulant drugs, antibiotic drugs or the like, fluid infusion, alimentation or the like.

(2) Keeping venous route (locating and securing) is essential for major operations, treatments in ICUs or CCUs or the like. In many cases, if intravascular injection is urgently needed in the cases described in (1), peripheral vessels may have collapsed because of a pressure reduction or a reduction of blood flow and any injection cannot be made thereto. Therefore, before the patient is in an emergency condition, an appropriate peripheral vessel has been selected and a normal saline solution is continuously infused thereto, thereby providing for an emergency.

(3) Medical care for elderly people. In particular, debilitated elderly patients, patients with a cerebral vascular accident or the like are not capable of oral administration of drugs. Therefore, a continuous intravenous drip infusion is often used.

In addition, the cases (4) and (5) described below are not injection, but require puncture on a blood vessel. They are often performed in the clinical setting.

(4) Dialysis. Dialysis has been increasingly conducted. In dialysis, blood is led from an artery in the inner side of a bent elbow of a patient to a dialysis unit, and the blood after dialysis is returned to a vein in the same area. Here, to prepare the blood circuit, the blood vessels have to be punctured. In not a few cases, an obstruction or the like may occur in the blood circuit, and then, another blood circuit has to be newly prepared by changing the points of puncture. In addition, in many cases, a patient requiring dialysis have to be continuously subject to dialysis throughout his/her life. Therefore, the blood vessel wall and the periphery thereof at the area gradually become thicker and hardened, and thus, it becomes difficult to puncture the blood vessel.

(5) In many cases of cardiac catheterization or the like, the catheter is inserted into the femoral artery or vein. In this process, a mantle tube for guiding the catheter has to be inserted into the blood vessel in the first place. Since the mantle tube is thicker than the injection needle, if the mantle tube is inserted into the blood vessel unskillfully, the blood vessel is damaged heavily. Thus, in not a few cases, bleeding from the damaged blood vessel or the like causes treatments after the prolonged catheterization.

In the cases (4) and (5), puncture has to be carried out particularly accurately, and there is a need for means of facilitating puncture.

As described above, intravascular injection is repeatedly carried out for consecutive days for most inpatients for their respective cases. However, in many cases, in particular in the case of debilitated patients or female patients, a suitable blood vessel is often difficult to find in the body surface. In addition, the blood vessels are thickened and hardened due to scar formations because of injection needle insertions repeated for consecutive days, and thus, in many cases, the injection needle cannot readily reach the inside of the blood vessel even if repeatedly trying to insert the injection needle into the blood vessel. Therefore, the intravascular injection is highly painful to the patients, so that the doctors may often be puzzled what to do, and thus, there is a strong clinical need for measures to overcome such a difficulty.

However, in general, the efforts at developing devices are directed to expensive devices, such as PET and artificial organs, and requirements arising in the clinical setting have received little attention.

In order to improve such a circumstance, the prior art was investigated. However, such a technique that directly tackles the circumstance described above was not found. Techniques found that are considered to be somewhat associated with the present technique are listed in the following.

[Diagnosis of Vascular Hardness]

Conventionally, there has been used a diagnostic approach using an indicator (stiffness parameter) that indicates the healthiness of a blood vessel based on the relation between the diameter change and the pressure change resulting from pulsation of the artery (see non-patent reference 1, for example) or a diagnostic approach using an indicator that indicates a statistic change by aging of the blood vessel diameter (see non-patent references 2 and 3, for example). However, there is not found an approach of diagnosing the degree of hardening of a local site of a blood vessel. Ultrasound backscatter pattern analysis is considered to be effective in diagnosis of a local site of a blood vessel which has been hardened to be difficult to puncture. However, in conventionally tissue characteristic diagnostic approaches, backscatter pattern analysis is mainly carried out in vitro. As an in vivo approach, there has been an "integrated backscattering method" that diagnoses scarring of the cardiac muscle due to myocardial infarction (see non-patent reference 4, for example). However, this diagnostic approach cannot be applied as it is to evaluate the difficulty of puncture with an injection needle.

[Puncture assistant device]

Conventionally, for ultrasonic puncture assistant devices, ultrasonically guided puncture methods have been established and widely used (see patent references 1 to 3, for example). However, they are directed to objects located deeply below the body surface (kidney, liver, uterus or the like), rather than the blood vessel near the body surface as in the present invention.

Patent Reference 1
   Japanese Patent Laid-Open No. 11-151244
Patent Reference 2
   Japanese Patent Laid-Open No. 5-168636
Patent Reference 3
   Japanese Patent Laid-Open No. 7-184998
Non-Patent Reference 1
   Hasegawa M., et al.: Diagnosis of Carotid Arterial Lesions and Its Clinical Application—With Special Reference to Cerebral Circulation, Vol 35, No.6, P349–358, 1995

Non-Patent Reference 2

Yamazaki Y., et al.: Detection of early change in carotid arteriosclerosis by ultrasound high-resolution B-made imaging, Diabetes Journal vol. 23, No. 1, P25–27, 1995

Non-Patent Reference 3

Handa N., et al.: Ultrasonic Evaluation of Early Carotid Atherosclerosis, Stroke, Vol. 21, No.11, P1567–1572, 1990

Non-Patent Reference 4

J. G. Miller, et al.: MYOCARDIAL TISSUE CHARACTERIZATION: AN APPROACH BASED ON QUANTITATIVE BACKSCATTER AND ATTENUATION, IEEE ULTRASONIC SYMPOSIUM P782–793, 1983

SUMMARY OF THE INVENTION

The present invention has been made in view of the above circumstances and provides a puncture difficulty evaluating device that can readily evaluate the difficulty of puncture in a measurement point.

In order to attain the object described above, a puncture difficulty evaluating device has: an ultrasonic transmitting section that irradiates a measurement point of a specimen with an ultrasonic pulse; an ultrasound receiver section that receives the ultrasound backscattered at said measurement point and determines an integral of the power of the ultrasound over a predetermined angle range; a parameter generating section that generates a parameter indicating the difficulty of puncture in said measurement point based on the integral determined in said ultrasonic receiver section.

The puncture difficulty evaluating-device according to the present invention is based on a principle that a parameter indicating the difficulty of puncture is generated based on the integral of the ultrasound backscattered at the measurement point over the predetermined angle range. Determining the integral allows the puncture difficulty to be known readily.

In the puncture difficulty evaluating device according to the present invention, preferably, said ultrasonic receiver section determines a first integral of the power of the ultrasound backscattered at said measurement point over a first predetermined angle range and a second integral of the power of the ultrasound backscattered at said measurement point over a second predetermined angle range, and said parameter generating section generates said parameter based on both said first integral and said second integral determined in said ultrasonic receiver section.

In this way, since the two different integrals over different angle ranges (first integral and second integral) are determined, and the puncture difficulty is determined based on the both integrals, the puncture difficulty can be evaluated more accurately.

Here, in the implementation in which the first and second integrals are both determined, said parameter generating section may generate said parameter by determining the ratio between said first integral and said second integral. Alternatively, said parameter generating section may generate said parameter by determining the difference between said first integral and said second integral. Alternatively, said parameter generating section may generate said parameter by determining the ratio between the difference between said first integral and said second integral and the difference between said first angle and said second angle.

In the puncture difficulty evaluating device according to the present invention described above, once the parameter indicating the puncture difficulty is determined, the parameter itself may be presented to an operator so that the operator determines the puncture difficulty. However, rather than to make the operator determine the puncture difficulty, the puncture difficulty evaluating device according to the present invention preferably has a puncture difficulty determining section that determines the difficulty of puncture in said measurement point by comparing the parameter determined in said parameter generating section with a predetermined comparative evaluation reference value.

This allows the operator to know the puncture difficulty further readily.

In addition, the puncture difficulty evaluating device according to the present invention, said ultrasonic transmitting section may irradiate each measurement point with each ultrasonic pulse emitted from each ultrasonic transducer distant from the measurement point by such an amount that the measurement point lies in a far sound field. Alternatively, the puncture difficulty evaluating device according to the present invention may have plural ultrasonic transducers arranged, and said ultrasonic transmitting section emits, from the plural ultrasonic transducers, ultrasonic pulses whose phases are controlled for the ultrasonic pulses to be focused on a predetermined measurement point.

In addition, the puncture difficulty evaluating device according to the present invention, preferably, said ultrasonic transmitting section sequentially irradiates plural measurement points with ultrasonic pulses, said ultrasonic receiver section sequentially receives ultrasounds backscattered at the plural measurement points and sequentially determines integrals for the respective measurement points, and said parameter generating section generates a parameter indicating the difficulty of puncture in each of said plural measurement points.

Since measurement is carried out sequentially for the plural measurement points, sites which are easy to puncture can be found in a shorter time.

Furthermore, the puncture difficulty evaluating device according to the present invention preferably has a B-mode image generating section that transmits an ultrasonic pulse to the specimen, receives an ultrasound backscattered in the specimen and generates a B-mode image, and an image display section that displays the B-mode image and an indication of the difficulty of puncture at the measurement point on the B-mode image, the indication being generated based on the parameter generated in said parameter generating section.

Since the puncture difficulty is associated with the measurement points on the B-mode image to be displayed, sites which are easy to puncture can be readily recognized visually.

Furthermore, preferably, the puncture difficulty evaluating device according to the present invention has an ultrasonic probe for transmitting and receiving an ultrasound, said ultrasonic transmitting section irradiates the measurement point with an ultrasonic pulse from the ultrasonic probe, and said ultrasonic receiver section receives the backscattered ultrasound at the ultrasonic probe.

Compared to the case where a transmitting ultrasonic probe and a receiving ultrasonic probe are provided separately, the transmitting and receiving ultrasonic probe allows the whole probe size to be reduced, the precision to be enhanced and the flexibility of measurement to be increased.

Here, in the implementation in which the ultrasonic probe is provided, the puncture difficulty evaluating device preferably has a holding mechanism for holding said ultrasonic probe, and a guide mechanism that fixes the specimen and guides the movement of said holding mechanism, thereby guiding the movement of the ultrasonic probe supported by the holding mechanism along the specimen. In this case, preferably, said holding mechanism supports said ultrasonic probe in such a manner that the position of said ultrasonic probe can be adjusted in a direction toward or away from the specimen. Alternatively, it is also a preferred implementation that said holding mechanism supports said ultrasonic probe slidably in a direction crossing the direction in which the holding mechanism guided by said guide mechanism moves.

In this way, if the ultrasonic probe is held so that the movement of the ultrasonic probe is guided along the specimen, the ultrasonic probe can be moved in a desired direction along the specimen and the measurement point can be changed readily.

Furthermore, the puncture difficulty evaluating device preferably has a puncture guide mechanism that guides puncture into the specimen fixed to said guide mechanism.

Providing the puncture guide mechanism allows puncture to be made easily.

Furthermore, in the case where the puncture guide mechanism is provided, the puncture difficulty evaluating device preferably has a B-mode image generating section that transmits an ultrasonic pulse to the specimen fixed to said guide mechanism, receives an ultrasound backscattered in the specimen and generates a B-mode image, and an image display section that displays the B-mode image generated in said B-mode image generating section and displays, on the B-mode image, a destination point which is reached by the tip of a needle when the needle is guided by said puncture guide mechanism to a puncture terminal point in the specimen.

According to this implementation, the destination point of the tip of the needle guided by the puncture guide mechanism for puncture can be checked on the B-mode image before puncture, and therefore, it is possible to prevent puncture from failing and assure puncture in a desired site.

Furthermore, in the ultrasonic probe, preferably, said ultrasonic probe has plural ultrasonic transducers having front surfaces facing the specimen concaved along a first direction and arranged in a second direction crossing the first direction, a flexible acoustic coupler removably mounted on the front surfaces of the plural ultrasonic transducers, and an acoustic coupler attachment mechanism that removably attaches said flexible acoustic coupler to the front surfaces of said plural ultrasonic transducers.

The arrangement of the ultrasonic transducers having concave surfaces allows the ultrasound to converge into a smaller spot at the measurement, thereby increasing the measurement resolution.

BRIEF DESCRIPTION OF THE DRAWINGS

Preferred embodiments of the present invention will be described in detail based on the following figures, wherein:

FIG. 6 schematically shows differences P(Δθ) between two integrals of SIBV(θ1) and SIBV(θ2);

DETAILED DESCRIPTION OF THE PREFERRED EMBODIMENTS

In the following, embodiments of the present invention will be described.

Figure 1:
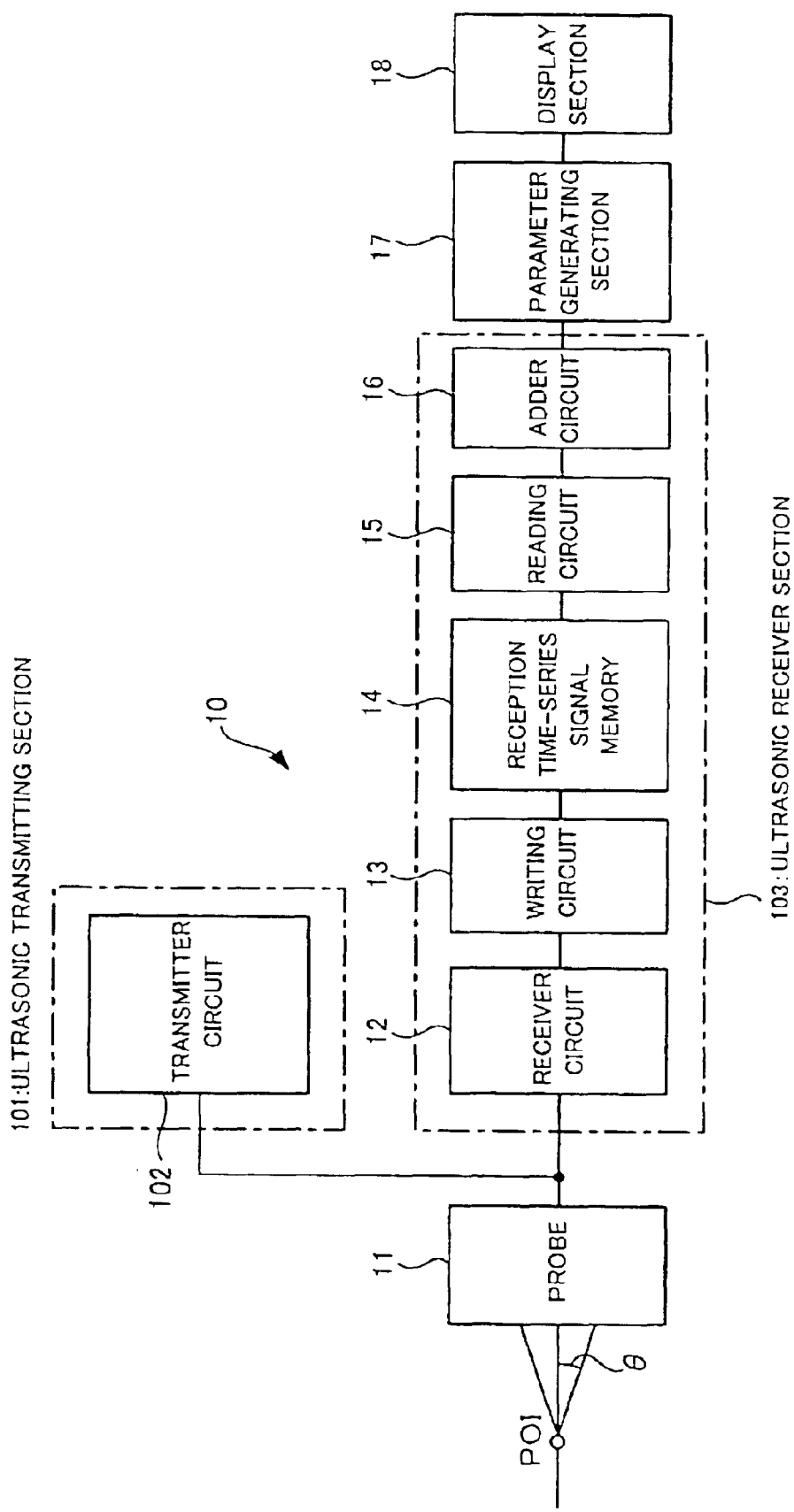
FIG. 1 is a block diagram showing an embodiment of a puncture difficulty evaluating device according to the present invention.

FIG. 1 is a block diagram showing an embodiment of a puncture difficulty evaluating device according to the present invention.

In a puncture difficulty evaluating device 10 shown in FIG. 1, a transmitter circuit 102 in an ultrasonic transmitting section 101 outputs a driving pulse to an ultrasonic probe 11. The ultrasonic probe 11 transmits an ultrasound to a point of interest (POI). The ultrasonic probe 11 has an array of 128 ultrasonic transducers, for example, and the ultrasound is transmitted to the POI from all or some of the ultrasonic transducers.

The ultrasound reflected at the POI is picked up by the ultrasonic transducers arranged in the ultrasonic probe 11, and the resulting signals are received by a receiver circuit 12 of an ultrasonic receiver section 103.

An echo signal, which results from the reception of the ultrasound by the receiver circuit 12, is temporarily stored in a received time-series signal memory 14 by a writing circuit 13 in a time series manner, and then read therefrom by a reading circuit 15. Then, the signals obtained in the ultrasonic transducers located within a range defined by a predetermined angle with respect to the line from the POI to the ultrasonic probe 11 (within a range of an angle 2θ defined by a half angle θ in FIG. 1) are added to each other with being in phase with each other, by an adder circuit 16. In this way, the integral value of the powers of the ultrasounds reflected off the POI with respect to the range defined by the predetermined angle (half angle of θ) is obtained. The integral value is input to a parameter generating section 17, and the parameter generating section 17 calculates a parameter which serves as an indicator for evaluating the difficulty of puncture in the POI. The calculated parameter is transmitted to a display section 18, where the difficulty of puncture in the POI is displayed in the form of a numeric value, an image (luminance or color) or the like.

Figure 2:
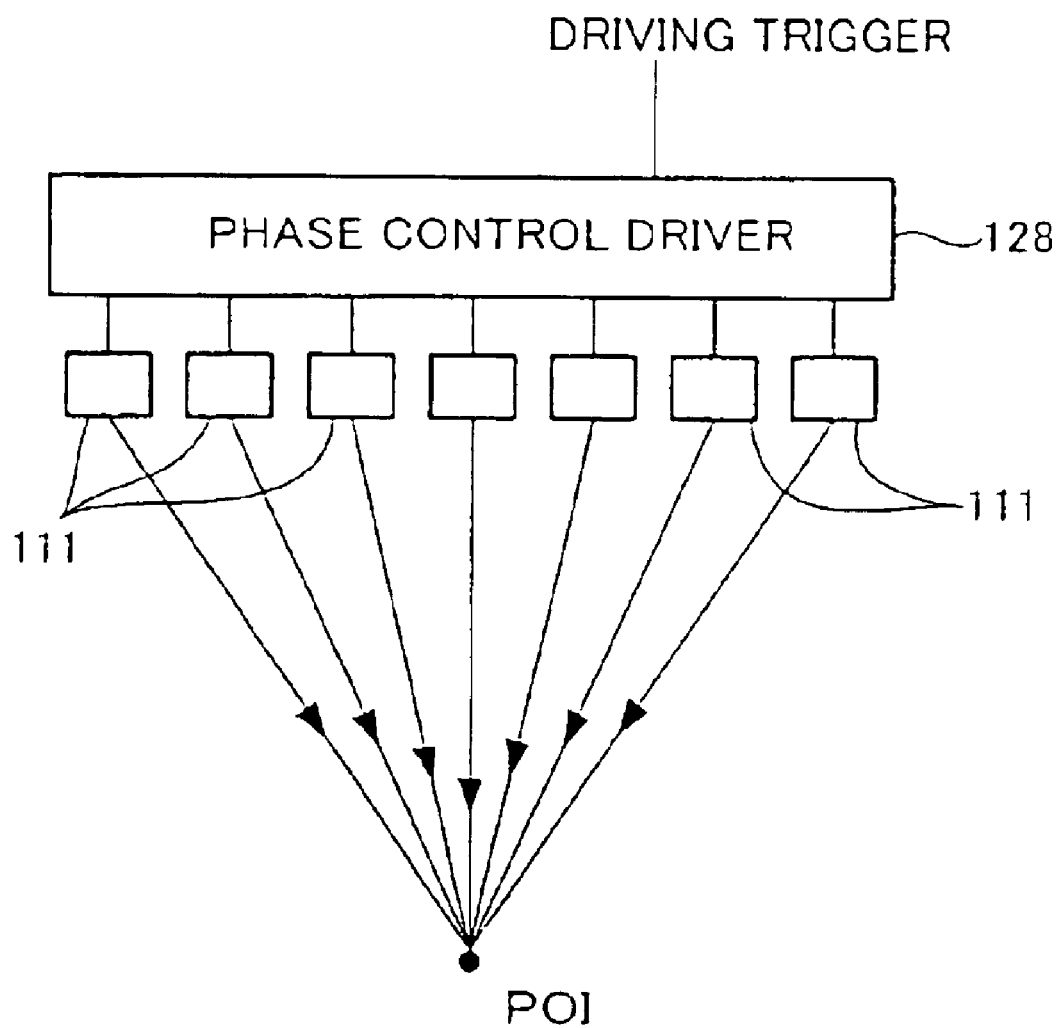
FIG. 2 is a diagram for illustrating a principle of ultrasound transmission.

FIG. 2 is a diagram for illustrating a principle of ultrasound transmission.

The transmitter circuit 102 of the puncture difficulty evaluating device 10 in FIG. 1 has a phase controlling driver 128, and the ultrasonic probe 11 has an array of plural ultrasonic transducers 111 (for simplicity, only seven ultrasonic transducers are shown). In transmission of an ultrasound to the POI, in response to receiving a driving trigger pulse which indicates transmission of an ultrasonic pulse, the phase controlling driver 128 sends driving pulses to the plural ultrasonic transducers responsible for ultrasound transmission (all of the seven ultrasonic transducers 111 in FIG. 2) at such timings that the ultrasonic pulses emitted from the ultrasonic transducers 111 arrive at the POI simultaneously, thereby causing the ultrasonic transducers 111 to transmit ultrasonic pulses. In this way, a transmission ultrasonic beam which is focused on the POI is formed.

Figure 3:
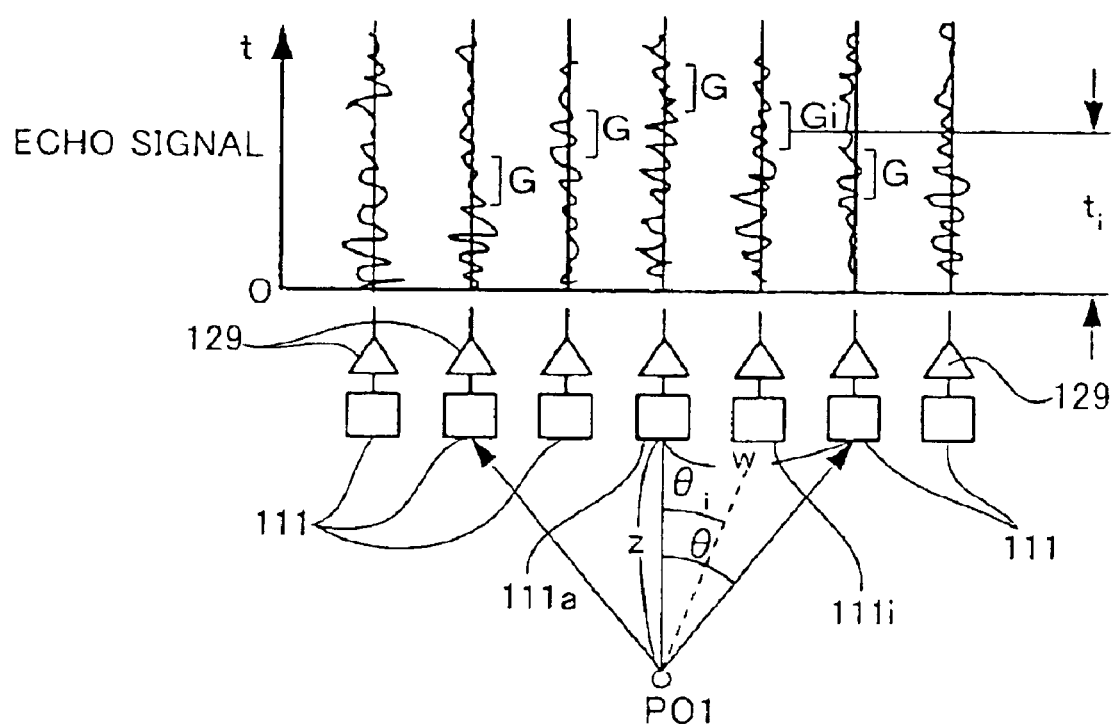
FIG. 3 is a diagram for illustrating a principle of determining an integral value.

FIG. 3 is a diagram for illustrating a principle of determining an integral value.

The ultrasound reflected off the POI is picked up by the large number of ultrasonic transducers 111 arranged in the ultrasonic probe 11 (for simplicity, only seven transducers are shown in FIG. 3), and then amplified by amplifiers 129 provided in the receiver circuit 12 of the puncture difficulty evaluating device 10 in FIG. 1 and associated with their respective ultrasonic transducers 111. Received signals thus obtained are temporarily stored in the received time-series signal memory 14 by the writing circuit 13 shown in FIG. 1, and then read therefrom by the reading circuit 15. Since the distances to the POI vary among the ultrasonic transducers 111 as shown in FIG. 3, in reading by the reading circuit 15, the reading circuit reads echo signals received by the ultrasonic transducers 111 partially in accordance with the times at which the ultrasounds transmitted by the ultrasonic transducers and reflected off the POI arrive at the respective ultrasonic transducers 111.

Specifically, provided that the distance between the POI and a center ultrasonic transducer 111a closest to the POI is z, the angle between the line segment connecting the center ultrasonic transducer 111a and the POI and the line segment connecting the POI and an i-th ultrasonic transducer 111i is θi, and the addressing distance to the center of a gate Gi for which the echo signal obtained in the i-th ultrasonic transducer 111i is extracted is ti as shown in FIG. 3, the reading circuit 15 reads the echo signal within the range of the gate Gi defined by the following formula (1):

$$ti = (z + z/\cos\theta i)/C \quad (1)$$

where reference character C denotes the sound velocity.

Here, the reading circuit 15 reads only the echo signals obtained in the ultrasonic transducers 111 located within the range defined by the deflection angle ±θ from the POI, and the adder circuit 16 adds the signal parts within the respective gates G to each other with the leading edges thereof temporally aligned with each other. This addition is expressed by the following formula (2):

$$SIBV(\theta) = \sum_{i=0}^{\pm n} Si \quad (2)$$

where reference character Si denotes an echo signal part within a gate Gi for an i-th ultrasonic transducer, and reference character ±n denotes the number of the transducer located at the position defined by the angle ±θ.

The sum value SIBV (specially integrated backscatter value) is equivalent to the value which is referred to as the integral herein, and expressed as SIBV(θ) herein to make it clear that the value is the integral (sum) for the angle range of ±θ.

Expressing the formula (2) in the form of integral results in the formula (3):

$$SIBV(\theta) = \int_{-\theta}^{\theta} S(\theta)d\theta \quad (3)$$

where S(θ) denotes an echo signal in the direction of the angle θ.

Based on the integral (sum) SIBV determined by the formula (2) or (3), the parameter generating section 17 in FIG. 1 determines a parameter which indicates the tissue characteristics of the POI, that is, the difficulty of puncture in the POI.

Figure 4:
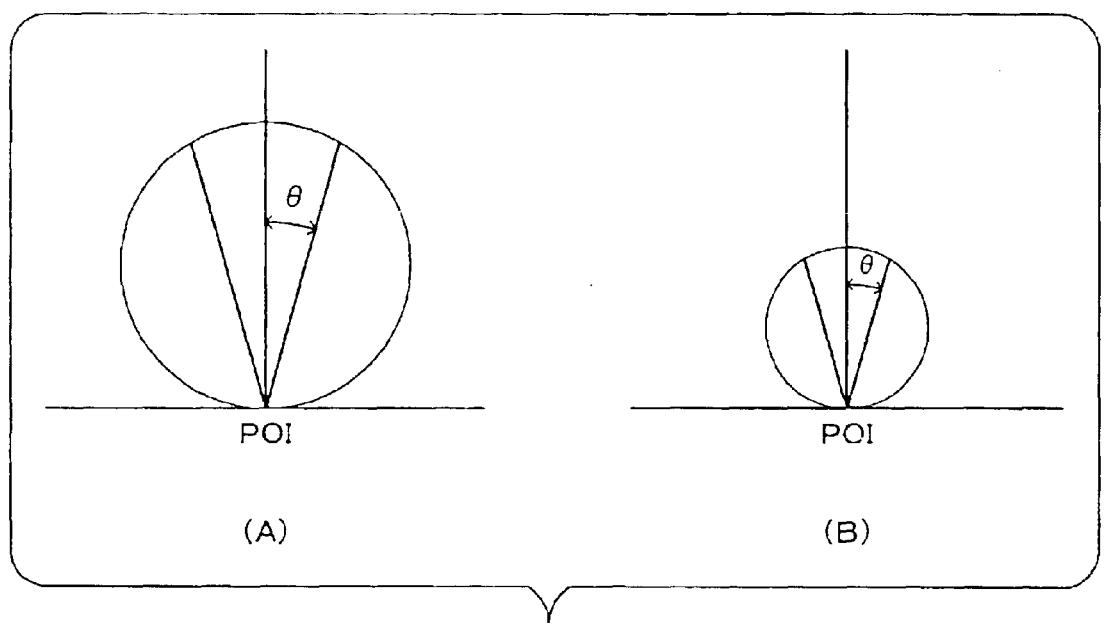
FIG. 4 shows variations of values of SIBV(θ) depending on a scattering intensity at a POI.

FIG. 4 shows variations of the value of SIBV(θ) depending on the scattering intensity at the POI.

Part (A) of FIG. 4 schematically shows a case where scattering at the POI is intense, and part(B) of FIG. 4 schematically shows a case where scattering at the POI is weak. Determining the integral for the angle range of ±θ of the backscattering at the POI can determine the integral SIBV(θ) for the scattering intensity. And based on the integral SIBV(θ), the tissue characteristic of the POI, that is, the difficulty of puncture in the POI can be evaluated.

According to the simplest implementation, the parameter generating section 17 in FIG. 1 may adopt the SIBV(θ) thus obtained as a parameter, passing the SIBV(θ) therethrough as it is. However, preferably, another parameter is calculated in accordance with any of the parameter calculation methods described below.

The value SIBV(θ) serving as a parameter or a parameter calculated as described below is transmitted to the display section 18, where the parameter is displayed in the form of a numeric value or a color corresponding to the parameter by being superposed on a B-mode image.

In the following, methods of calculating a parameter will be described.

Figure 5:
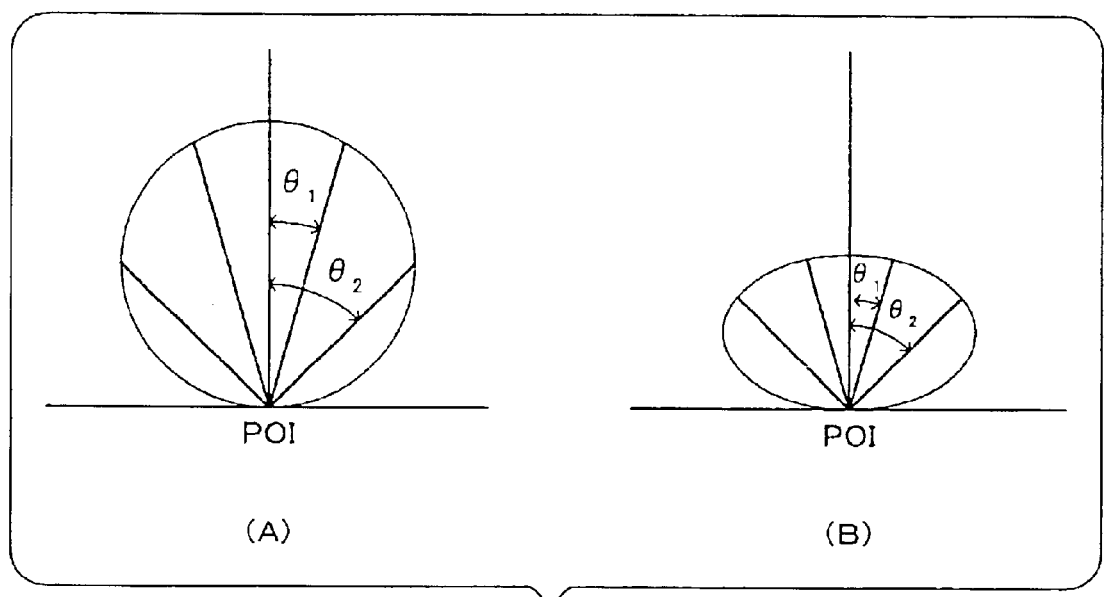
FIG. 5 is a schematic diagram showing variations of scattering patterns.

FIG. 5 is a schematic diagram showing variations of scattering patterns.

While only the scattering intensity is noted in FIG. 4, the variations of the scattering patterns are also significant information for evaluating the difficulty of puncture.

The scattering pattern shown in part (A) of FIG. 5 is substantially circular, and the scattering pattern shown in part (B) of FIG. 5 is an ellipse horizontally elongated. Besides, part (A) of FIG. 5 shows a wholly intense scattering and part (B) of FIG. 5 shows a wholly weak scattering.

To remove the information about the scattering intensity and to extract the information about the scattering pattern under such a condition, it is effective to normalize the value SIBV(θ) with the total backscattering intensity to determine the value SIBV(θ, 90), which is expressed by the following formula (4):

$$SIBV(\theta, 90) = \frac{\int_{-\theta}^{\theta} S(\theta)d\theta}{\int_{-90}^{90} S(\theta)d\theta} \quad (4)$$

However, in an in vivo situation in which a living body such as human body is used as a specimen, the total backscattering intensity is difficult to obtain. Thus, in this specification, two values of SIBV(θ1) and SIBV(θ2) which are different in integral range are determined, and the ratio between the values is determined and used as a parameter P(θ1, θ2) which serves as an indicator of the scattering pattern.

$$P(\theta1, \theta2) = \frac{SIBV(\theta1)}{SIBV(\theta2)} = \frac{\int_{-\theta1}^{\theta1} S(\theta)d\theta}{\int_{-\theta2}^{\theta2} S(\theta)d\theta} \quad (5)$$

That is, the adder circuit 16 in FIG. 1 determines the two integral of SIBV(θ1) and SIBV(θ2) and transmits them to the parameter generating section 17. The parameter generating section 17 determines the parameter P(θ1, θ2) based on the above formula (5). The parameter P(θ1, θ2) may be used as a parameter to indicate the difficulty of puncture in the POI.

The difference P(Δθ) between the values SIBV(θ1) and SIBV(θ2), that is, $$P(\Delta\theta) = SIBV(\theta2) - SIBV(\theta1) \quad (6)$$

may also be used as an indicator of the scattering pattern. Thus, the adder circuit 16 in FIG. 1 may determine the two integrals of SIBV(θ1) and SIBV(θ2) and transmit them to the parameter generating section 17, and the parameter generating section 17 may determine the difference P(Δθ) and adopt the difference P(Δθ) as a parameter to indicate the difficulty of puncture.

Figure 6:
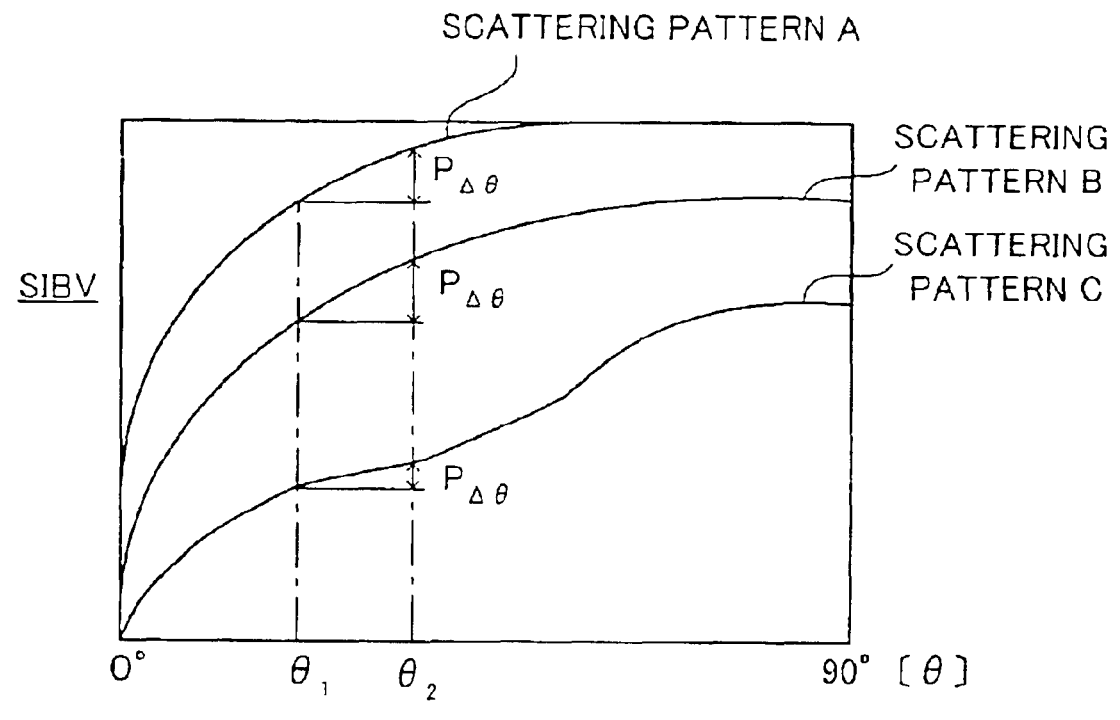

FIG. 6 schematically shows differences P(Δθ) between the two integrals of SIBV(θ1) and SIBV(θ2).

The horizontal axis indicates the angle θ, and the vertical axis indicates the integral SIBV(θ) for the angle range of ±θ. Three curves of scattering patterns A, B and C correspond to the scattering patterns shown in part (A) of FIG. 4 (part (A) of FIG. 5 shows the same scattering pattern and scattering intensity), part (B) of FIG. 4 and part (B) of FIG. 5, respectively.

As for the differences P(Δθ) determined for the scattering patterns A (part (A) of FIG. 4), B (part (B) of FIG. 4) and C (part (B) of FIG. 5), depending on selection of the angles θ1 and θ2, the differences P(Δθ) for the scattering patterns A and B, which are substantially the same, approximate to each other, and the difference P(Δθ) for the scattering pattern C (part (B) of FIG. 5), which is significantly different from the other patterns, is significantly different from those for the other patterns.

In this way, the difference P(Δθ) between the two integrals of SIBV(θ1) and SIBV(θ2) can also serve as an indicator to indicate the variations of scattering patterns at the POI, and therefore, can serve as a parameter to indicate the difficulty of puncture in the POI.

Figure 7:
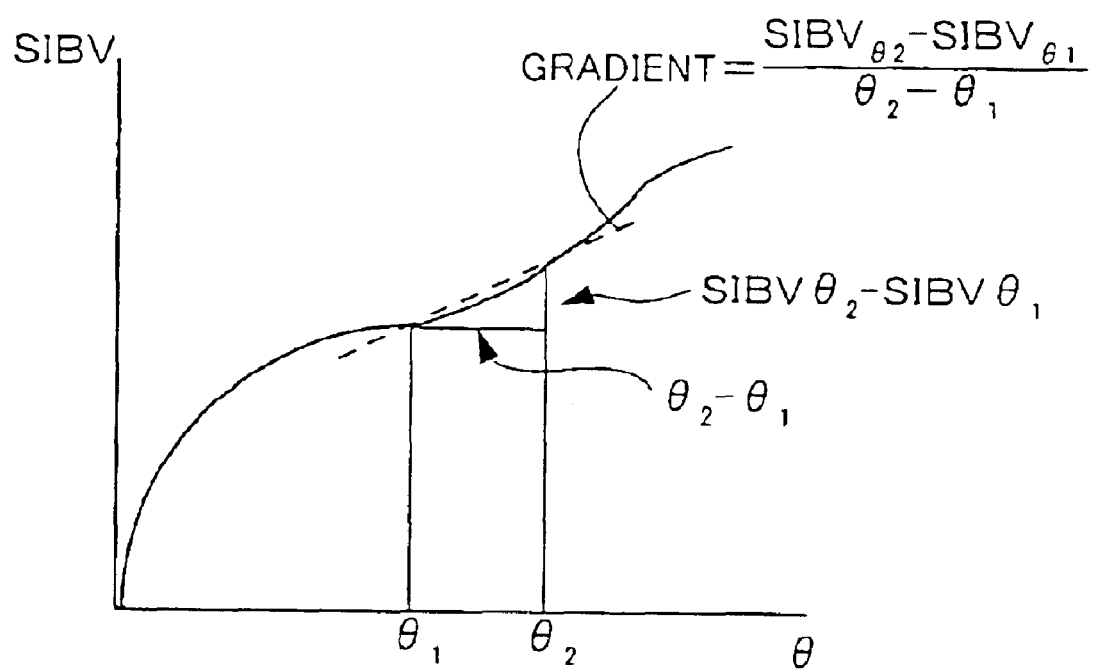
FIG. 7 is a graph showing the integral SIBV (vertical axis) with respect to the angle θ for a scattering pattern (horizontal axis)

FIG. 7 is a graph showing the integral SIBV (vertical axis) with respect to the angle θ for a scattering pattern (horizontal axis).

In addition to those described above, the gradient of the integral SIBV [dP(θ)/dθ] (θ1, θ2) shown in FIG. 7, which is expressed by the following formula (7), also indicates a characteristic of the scattering pattern, and thus, can serve as a parameter to indicate the difficulty of puncture in the POI.

$$[dP(\theta)/d\theta](\theta1, \theta2) = \frac{SIBV(\theta2) - SIBV(\theta1)}{\theta2 - \theta1} \quad (7)$$

Figure 8:
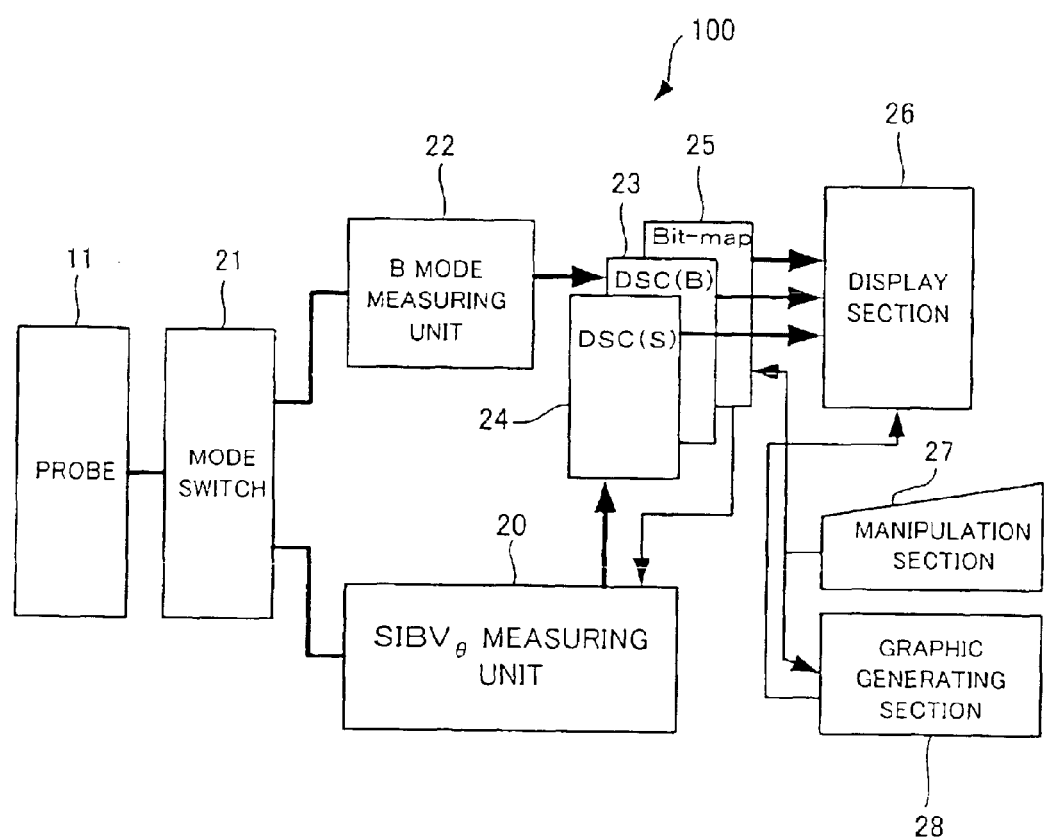
FIG. 8 is a circuit block diagram showing a variation of the puncture difficulty evaluating device shown in FIG. 1.

FIG. 8 is a circuit block diagram showing a variation of the puncture difficulty evaluating device 10 shown in FIG. 1.

Besides the ultrasonic probe 11 shown in FIG. 1, FIG. 8 shows an SIBV(θ) measuring unit 20, a mode switch 21, a B-mode measuring unit 22, a B-mode digital scan converter DSC (B) 23, an SIBV digital scan converter DSC (S) 24, an ROI (region of interest) information storing bit map 25, and a display section 26, a manipulation section 27 and a graphic generating section 28.

The mode switch 21 is to dynamically switch between modes in which the ultrasonic probe 11 transmits and receives an ultrasound for B-mode measuring and in which the ultrasonic probe 11 transmits and receives an ultrasound for SIBV(θ) measuring.

The B-mode measuring unit 22 is to apply an ultrasound transmission driving pulse to the ultrasonic probe 11 via the mode switch 21 to make it transmit an ultrasound into the specimen, amplify the echo signal obtained by the ultrasonic probe 11 picking up the ultrasound reflected at the inside of the specimen, perform a signal processing such as dynamic focusing on the echo signal to obtain information for each scan line, and write the information to the DSC (B) 23. One frame of B-mode image signal is obtained by repeating such transmission, reception and writing to the DSC (B) 23, converted into a signal suitable for display on the display section 26 and transmitted to the display section 26, whereby the B-mode image is displayed on the display section 26. The B-mode image display technique relates to fields including ultrasonic diagnosis equipment and have been used widely. Therefore, further detailed description thereof will be omitted.

On the other hand, the SIBV(θ) measuring unit 20 has an arrangement identical to the arrangement of the ultrasonic transmitting section 101, the ultrasonic receiver section 103 and the parameter generating section 17 shown in FIG. 1. The SIBV(θ) measuring unit 20 is to apply a driving pulse to the ultrasonic probe 11 via the mode switch 21 to make it transmit a ultrasonic pulse to the POI, amplify the echo signal reflected at the POI and picked up by the ultrasonic probe 11, and calculate the SIBV(θ) as described above.

Here, an operator manipulates the manipulation section 27 to specify a region of interest (ROI), which is a set of points of interest (POIs) for which the SIBV(θ) is to be measured, on the B-mode image displayed on the display section 26. The ROI specification information is stored in the bit map 25. Regarding each point in the specified ROI as a POI based on the ROI specification information from the bit map 25, the SIBV(θ) measuring circuit 20 transmits an ultrasound, receives the reflected ultrasound and calculates the SIBV(θ) for each POI. The values of SIBV(θ) calculated for the POIs in the ROI are temporarily stored in the DSC(S) 24, converted into a data form suitable for display on the display section 26 by the DSC (S) 24 and transmitted to the display section 26. For the inside of the ROI specified via the manipulation section 27, the display section 26 displays the SIBV(θ) measurements by superposing them on the B-mode image (monochrome image) by coloring. The graphic generating section 28 generates a cursor or other graphics in response to manipulation of the manipulation section 27, and the graphics generated by the graphic generating section 28 are also displayed on the display section 26 by superposing.

Figure 9:
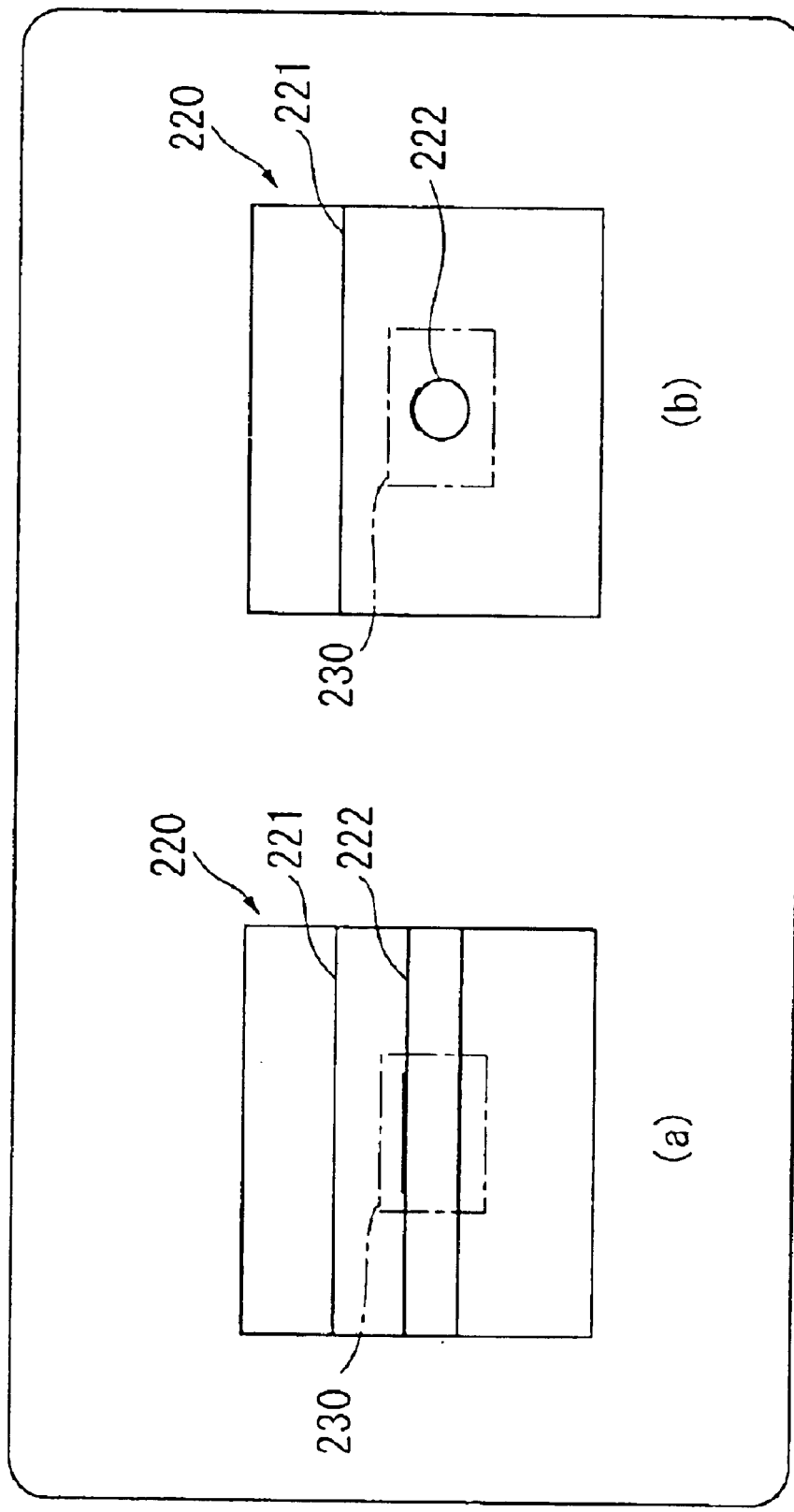
FIG. 9 shows examples of the image displayed on a display section shown in FIG. 8.

FIG. 9 shows an example of an image displayed on the display section 26 shown in FIG. 8.

In this example, the specimen is a part of a human arm. In a B-mode image 220 shown in part (A) of FIG. 9, an arm surface 221 and a blood vessel 222 extending horizontally below the arm surface can be seen. If an ROI 230 is specified on the B-mode image 220 via the manipulation section 27 shown in FIG. 8, values of SIBV(θ) are displayed at points in the ROI 230 by their respective associated colors. Thus, it is possible to find a part of the surface of the blood vessel 222 which is enough hardened to be difficult to puncture or a part thereof which is easy to puncture.

Part (B) of FIG. 9 is a schematic view of the B-mode image viewed along a direction which allows the cross section of the blood vessel 222 to be seen. The circular blood vessel 222 is shown below the arm surface 221, and the ROI 230 is specified so as to surround the blood vessel 222.

In this view, the difficulty of puncture for the cross section of the blood vessel 222 shown in the B-mode image 220 can be determined. As described later, moving the ultrasonic transducers relative to the arm (specimen) along the length of the blood vessel 222 to sequentially display different cross-sectional B-mode images can determine the difficulty of puncture in local sites of the blood vessel 222.

Figure 10:
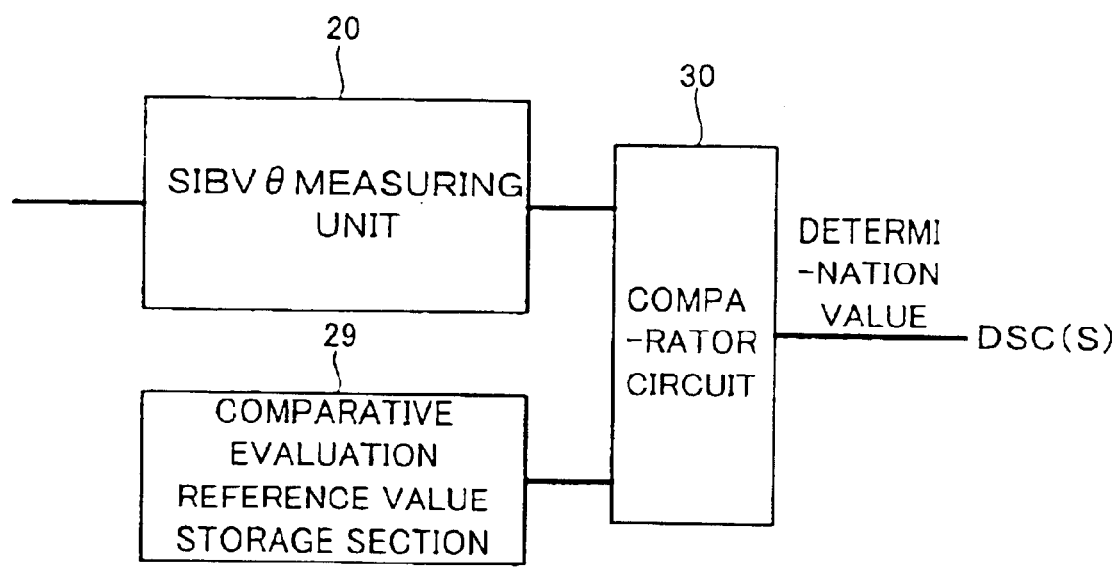
FIG. 10 is a partial circuit diagram showing a variation of the embodiment shown in FIG. 8.

FIG. 10 is a partial circuit diagram showing a variation of the embodiment shown in FIG. 8.

In the example shown in FIG. 8, the value of SIBV(θ) determined in the SIBV(θ) measuring unit 20 is input to the DSC (S) 24 as it is and is displayed on the display section 26 by a color associated therewith. However, in the example shown in FIG. 10, there are additionally provided a comparative evaluation reference value storage section 29 and a comparator circuit 30. The comparative evaluation reference value storage section 29 stores a comparative evaluation reference value for SIBV(θ) for determination of the puncture difficulty. When a value of SIBV(θ) is determined in the SIBV(θ) measuring circuit 20, the comparator circuit 30 compares the magnitudes of the determined SIBV(θ) and the comparative evaluation reference value read from the comparative evaluation reference value storage section 29 with each other to determine the difficulty of puncture in the POI. The determination result, which indicates the puncture difficulty for each POI, is stored in the DSC(S) 24 shown in FIG. 8. Therefore, on the display section 26 shown in FIG. 8, there are displayed sites which are easy to puncture and sites which are difficult to puncture, distinguished in a binary manner by luminance, color or the like. In this case, there is no need for the operator to determine the puncture difficulty.

Figure 11:
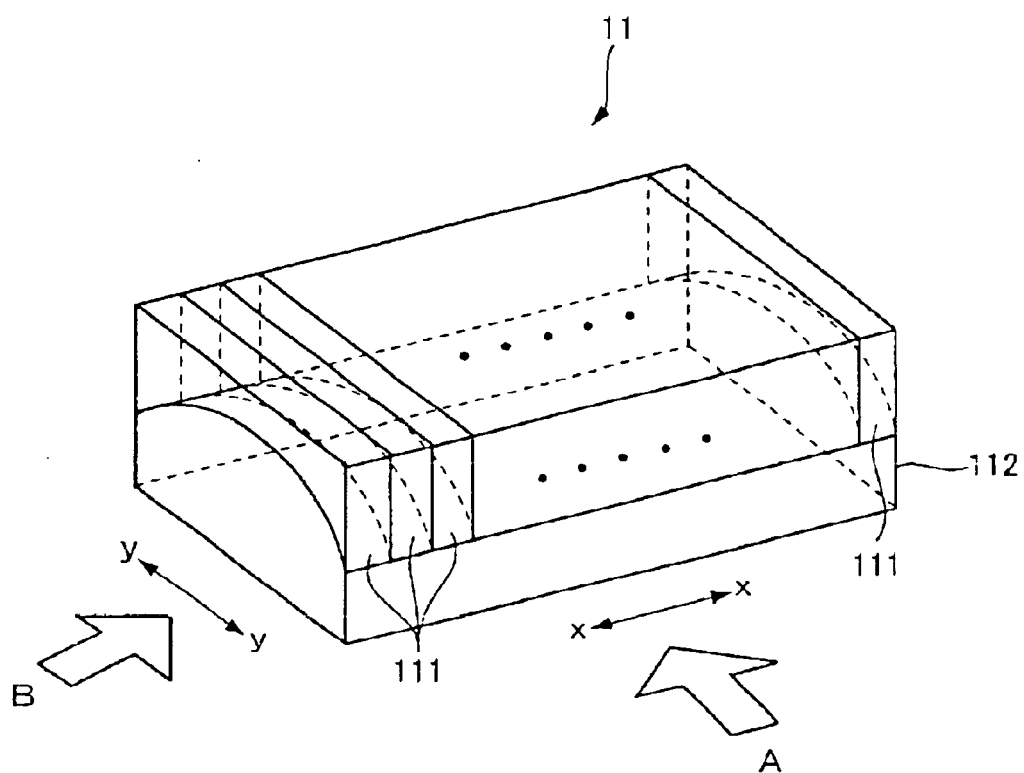
FIG. 11 shows a large number of ultrasonic transducers constituting an ultrasonic probe.

FIG. 11 shows a large number of (128, for example) ultrasonic transducers constituting the ultrasonic probe.

In the ultrasonic probe 11, 128 ultrasonic transducers 111 are arranged, for example.

Each ultrasonic transducer 111 has a front surface facing the specimen (bottom side in FIG. 11) concaved along the width (y—y direction in FIG. 11) perpendicular to the arrangement direction thereof (x—x direction in FIG. 11).

A flexible ultrasonic acoustic coupler 112 is removably attached to the front surfaces of the arranged ultrasonic transducers 111. When a driving pulse is applied to an ultrasonic transducer 111, the ultrasonic transducer 111 having received the driving pulse transmits an ultrasound, which is further transmitted into the specimen via the ultrasonic acoustic coupler 112. Furthermore, the ultrasound reflected at the surface or inside of the specimen is picked up by the ultrasonic transducer 111 via the ultrasonic acoustic coupler 112.

Figure 12:
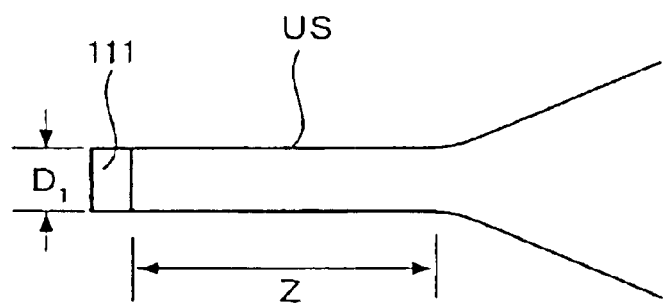
FIG. 12 shows an ultrasound beam emitted from one ultrasonic transducer, viewed along a direction perpendicular to an arrangement direction of ultrasonic transducers.

FIG. 12 shows an ultrasound beam emitted from one of the ultrasonic transducers 111 of the ultrasonic probe 11 shown in FIG. 11, viewed along the direction (y—y direction, indicated by arrow A in FIG. 11) perpendicular to the arrangement direction of the ultrasonic transducers 111 shown in FIG. 11.

The ultrasound beam emitted from the ultrasonic transducer 111 is less diffused in a near sound field closer to the ultrasonic transducer 111. Upon exiting the near sound field, the beam enters a far sound field and travels therein being diffused to some extent. Given that the distance from the ultrasonic transducer to the boundary between the near sound field and the far sound field is Z, the width of the ultrasonic transducer 111 is D, and the wavelength of the ultrasound is λ, the following formula (8) holds:

$$Z = \frac{D^2}{4\lambda} \tag{8}$$

For example, in the case of D=3 mm and λ=0.075 mm, Z=3²/(4×0.075)=30 (mm).

In the embodiment described above, in ultrasound transmission to a POI, plural ultrasonic transducers transmit ultrasounds by being adjusted so that the ultrasounds converge on the POI at the same time. However, in ultrasound transmission to a POI for determination of SIBV(θ), one ultrasonic transducer may transmit an ultrasound to each POI. However, in this case, the phase of the ultrasound is unstable in the near sound field within the distance Z shown in FIG. 12, and thus, the intensity of the reflected ultrasound is unstable in the near sound field. On the other hand, the phase of the ultrasound is stable in the far sound field, and thus, the ultrasound reflected at the POI can correctly reflect the characteristic of the POI. Therefore, when transmitting an ultrasound to a POI, it is preferred that the thickness of the like of the ultrasonic acoustic coupler 112 (see FIG. 11) is modified to locate the ultrasonic transducer at such a point that the POI lies within the far sound field.

Figure 13:
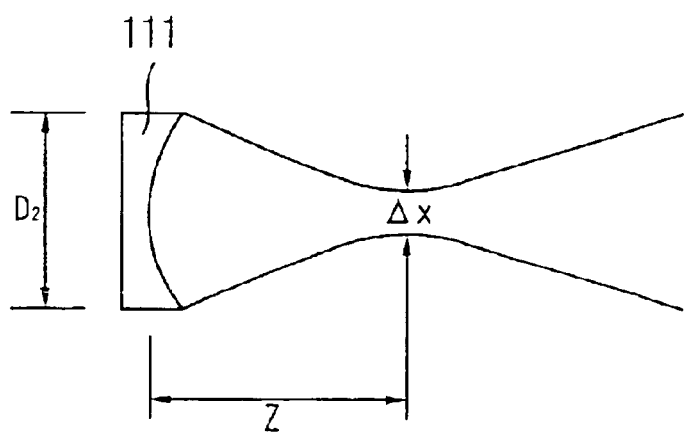
FIG. 13 shows an ultrasound beam emitted from one of the ultrasonic transducers 111 of the ultrasonic probe 11 shown in FIG. 11, viewed along the arrangement direction of the ultrasonic transducers shown in FIG. 11.

FIG. 13 shows an ultrasound beam emitted from one of the ultrasonic transducers 111 of the ultrasonic probe 11 shown in FIG. 11, viewed along the arrangement direction of the ultrasonic transducers shown in FIG. 11 (x—x direction, indicated by arrow B in FIG. 11).

When viewed along the arrangement direction (x—x direction), the ultrasonic transducer 111 has a concave front surface on the side of the specimen. An ultrasound 1111 transmitted from the ultrasonic transducer 111 travels toward the center of curvature of the concave curve and is focused on the center.

In the case of transmitting the ultrasound so as to be focused, the position of the ultrasonic transducer 111 is adjusted so that the POI is located at the focal point. At the focal point, ultrasounds are in phase, and stable reflected ultrasounds can be obtained. In addition, ultrasounds have a high power, and thus, measurement with a high S/N ratio can be performed.

Given that the width of the ultrasonic transducer 111 is D, the focal length of the ultrasound is Z, the ultrasound beam width at the focal point is Δx, and the wavelength of the ultrasound is λ, the following formula (9) holds:

$$\Delta x = \frac{\lambda Z}{D} \quad (9)$$

For example, in the case of D=10 mm, Z=20 mm and λ=0.075 mm, Δx=0.075×20/10=150×10$^{-3}$ mm.

In the example described above, one ultrasonic transducer with a concaved surface transmits an ultrasound which is to be focused. However, the same holds true for a case where timed driving pulses are applied to plural arranged ultrasonic transducers to make them transmit focused ultrasounds.

Figure 14:
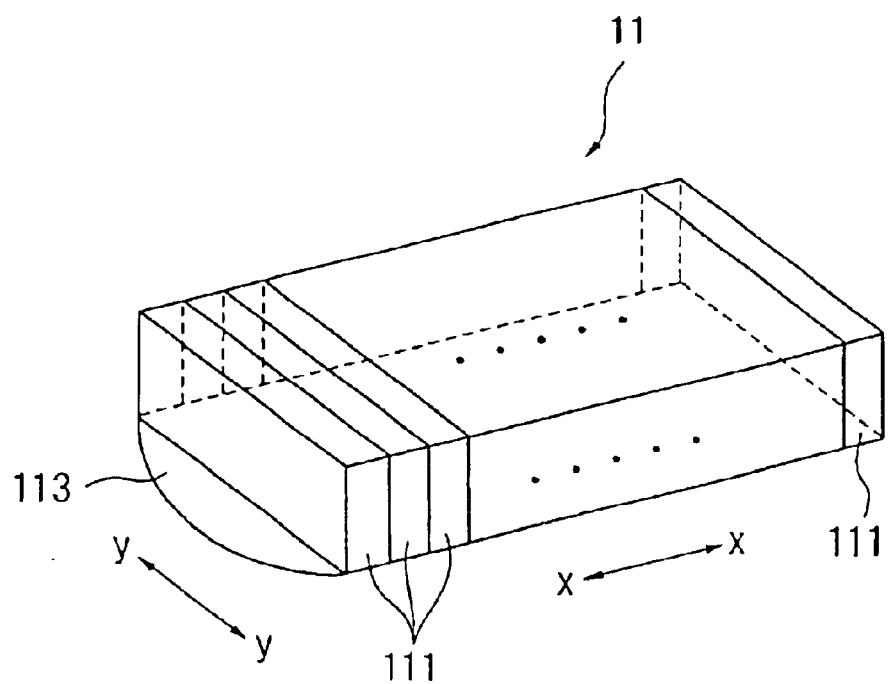
FIG. 14 shows an ultrasonic probe different from that shown in FIG. 11.

FIG. 14 shows an ultrasonic probe different from that shown in FIG. 11.

In this ultrasonic probe 11, ultrasonic transducers 111 having a flat front surface on the side of the specimen are arranged. On the front surfaces of the ultrasonic transducers 111, an acoustic lens 113 is disposed which focuses an ultrasound in a direction perpendicular to the arrangement direction of the ultrasonic transducers.

As in the case of the ultrasonic probe shown in FIG. 11, an ultrasonic acoustic coupler is mounted on the front surface of the acoustic lens 113. However, in FIG. 14, the ultrasonic acoustic coupler is not shown.

Figure 15:
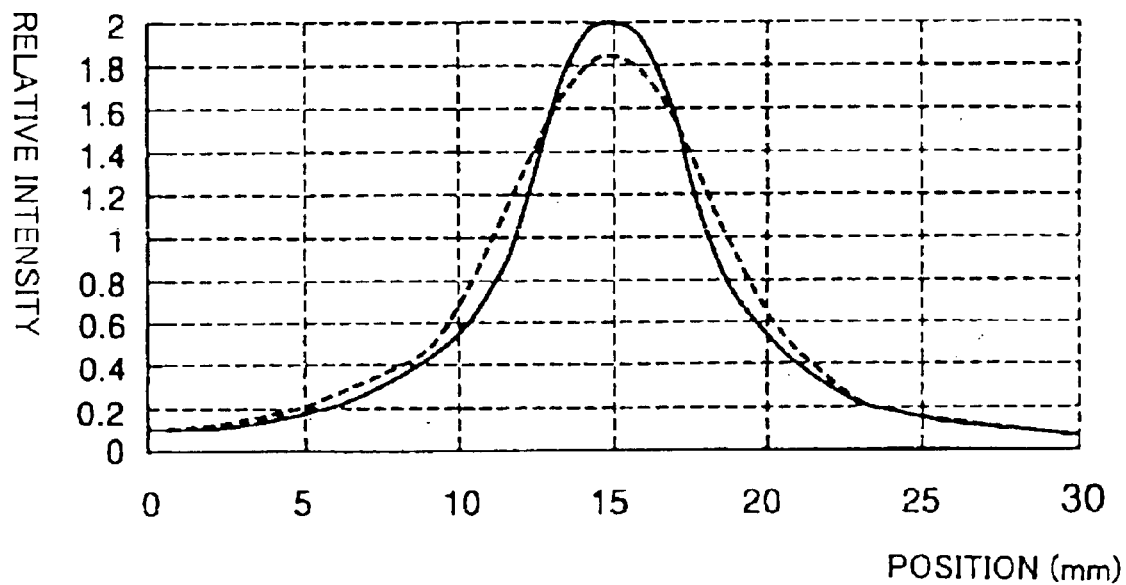
FIG. 15 shows profiles of ultrasound beams at their respective focal points.

FIG. 15 shows profiles of ultrasound beams at their respective focal points.

The solid line and the dashed line indicate the y—y direction profiles of the ultrasound beams at their respective focal points for the cases shown in FIGS. 11 and 14, respectively.

As can be seen from FIG. 15, the ultrasonic transducer having a concaved surface facing the specimen (FIG. 11) can provide a narrower beam diameter and a resolution increased accordingly.

Figure 16:
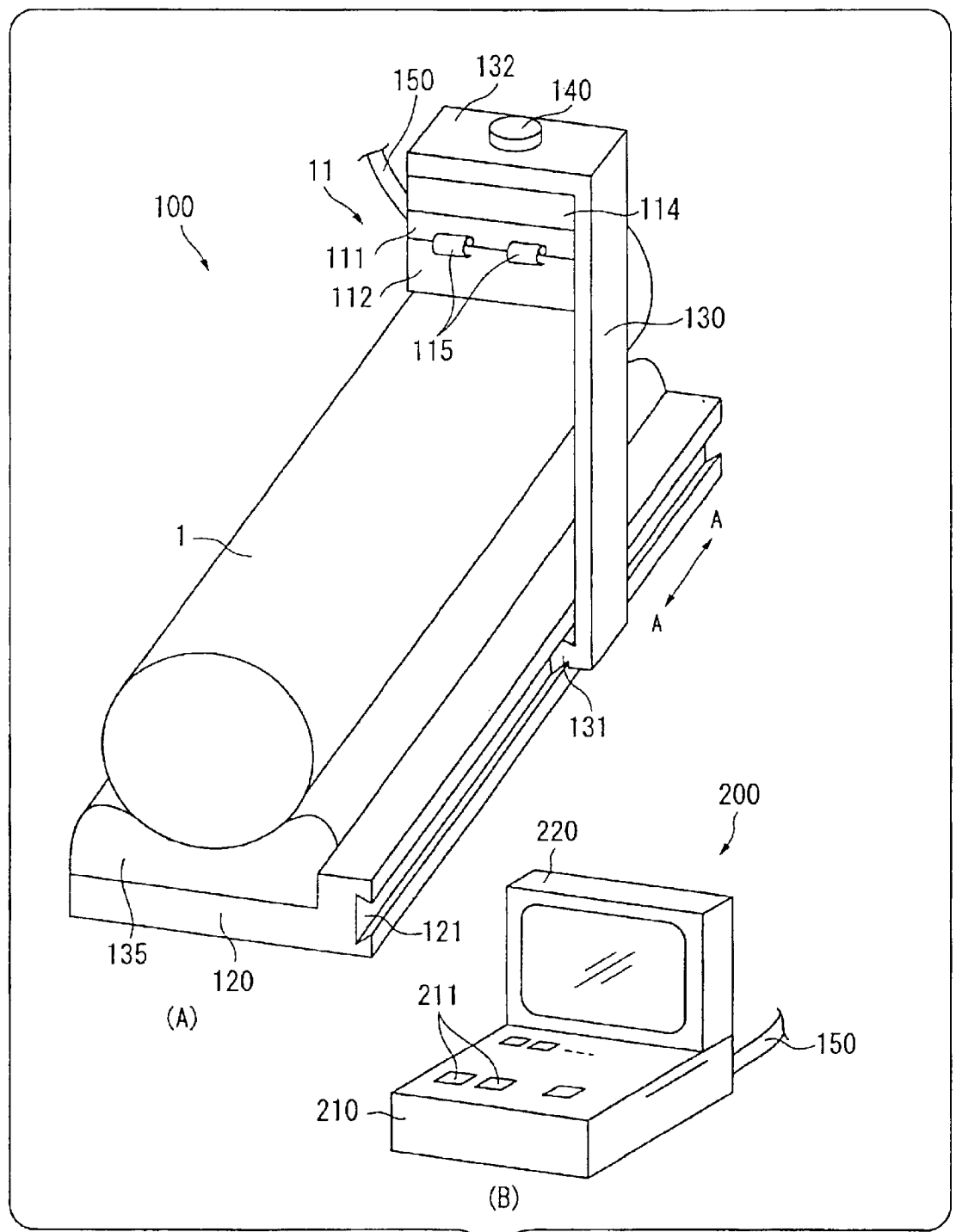
FIG. 16 is an outside view of a puncture difficulty evaluating device.

FIG. 16 is an outside view of a puncture difficulty evaluating device.

Part (A) of FIG. 16 shows a measuring section of the puncture difficulty evaluating device, and part (B) of FIG. 16 shows a main system section of the puncture difficulty evaluating device. In FIG. 16, the main system section is further scaled down than the measuring section.

A measuring section 100 shown in part (A) of FIG. 16 has a cushion 135 on amount 120, and a part of a human body to be punctured, such as human arm, (an arm 1 in this drawing) is placed on the cushion 135. In a side surface of the mount 120, an engagement recess 121 extending in the longitudinal direction of the arm 1 is formed. An engagement protrusion 131 formed in a lower part of a probe unit holder 130 engages with the engagement recess 121 slidably in the longitudinal direction of the arm 1 (direction indicated by arrow A—A). To a top board 132 of the probe unit holder 130, an ultrasonic probe 11 at a tip of an ultrasonic probe unit, which consists of the ultrasonic probe 11 and a cable 150, is fixed by an external thread 140 with a knob. The cable 150 is connected to the main system section 200 shown in part (B) of FIG. 16 via a connector (not shown). The structure of the ultrasonic probe 11 will be described later.

The main system section 200 shown in part (B) of FIG. 16 has a calculation section 210 and a display section 220, and various manipulation buttons 211 are provided on the top surface of the calculation section 210.

The main system section 200 shown in part (B) of FIG. 16 is equivalent to all the components shown in the block diagram in FIG. 1 except for the ultrasonic probe 11, that is, the ultrasonic transmitting section 101, the ultrasound transmitter circuit 102, the parameter generating section 17 and the display section 18. The calculation section 210 has integrated therein all these functional sections except for the display section 18. The display section 220 is equivalent to the display section 18 in FIG. 1.

The same holds true for the cases shown in FIGS. 8 and 10, and the main system section 200 is equivalent to the arrangement of all the functional sections except for the ultrasonic probe 11.

The main system section 200 shown in part (B) of FIG. 16 is connected, via a connector (not shown) and the cable 150, to the ultrasonic probe 11 fixed to the probe unit holder 130 of the measuring section 100 shown in part (A) of FIG. 16.

Figure 17:
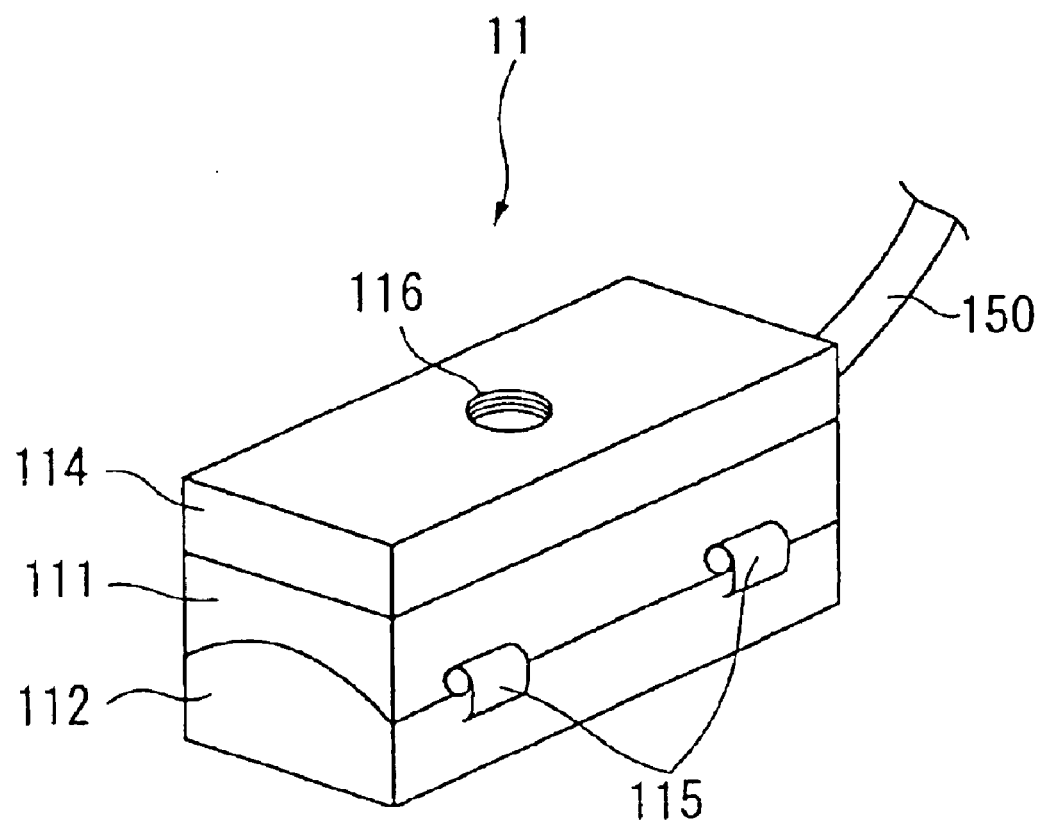
FIG. 17 is a perspective view of the ultrasonic probe shown in FIG. 16.

FIG. 17 is a perspective view of the ultrasonic probe shown in FIG. 16.

In this drawing, there is shown one ultrasonic transducer rather than separate ultrasonic transducers. However, in actual, plural (128, for example) ultrasonic transducers 111 are arranged as shown in FIG. 11, and the ultrasonic acoustic coupler 112 is removably attached to the front surfaces of the ultrasonic transducers by means of a holding mechanism 115. In addition, the array of the ultrasonic transducers 111 is supported on the base 114 at the back thereof. In addition, at the center of the base 114, there is formed an internal thread hole 116 into which the external thread with a knob is screwed.

Figure 18:
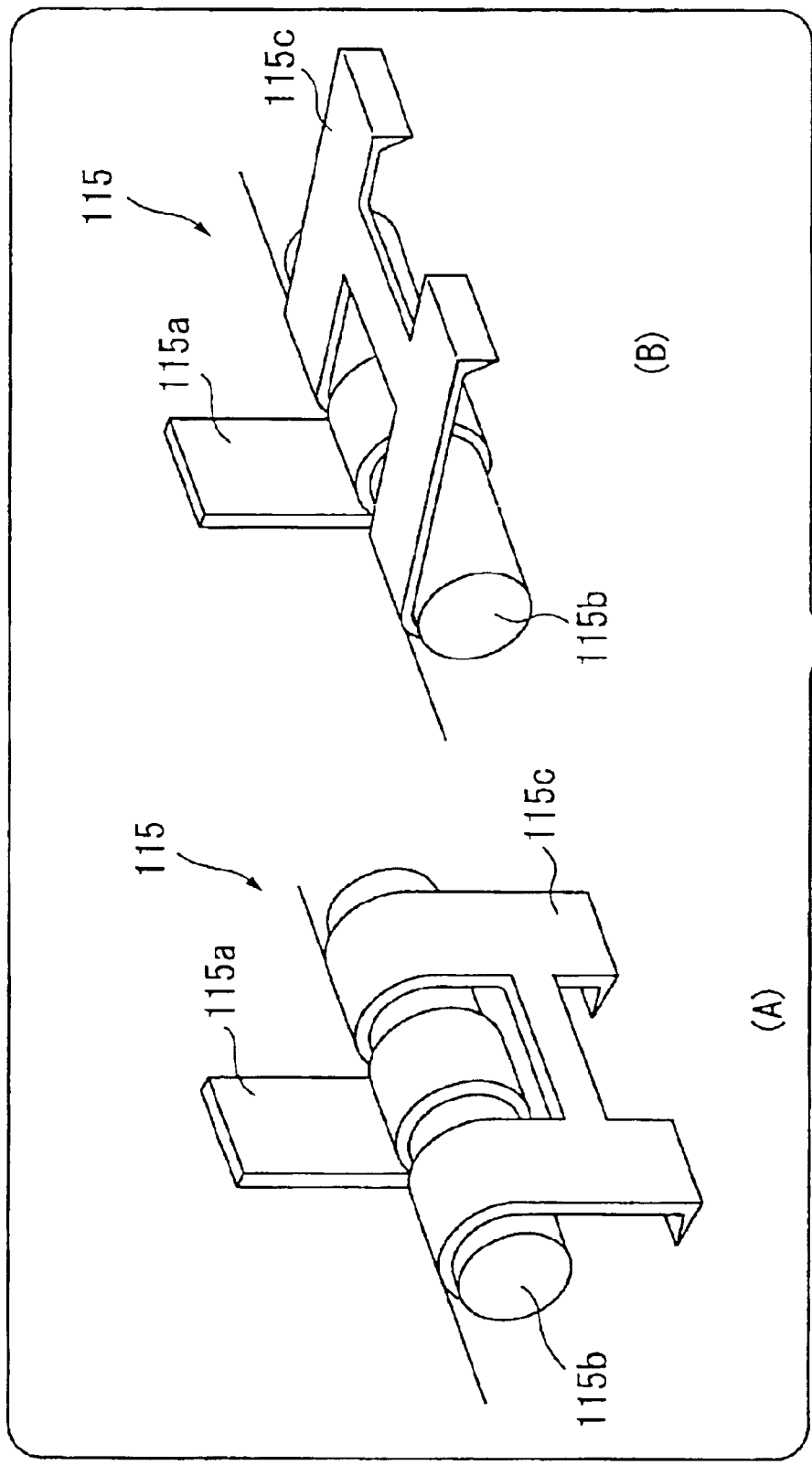
FIG. 18 shows an example of the arrangement of a holding mechanism for removably attaching an ultrasonic acoustic coupler.

FIG. 18 shows an example of the holding mechanism for removably attaching the ultrasonic acoustic coupler.

The holding mechanism 115 has a fixed section 115a which is fixed to a side wall of the ultrasonic transducer array, a pivot shaft 115b and a movable claw 115c pivotally movable relative to the fixed section 115a. When the ultrasonic acoustic coupler is to be attached to the front surface of the ultrasonic transducer array, the movable claw 115c is pivoted into a position shown in part (A) of FIG. 18. Then, the tip of the movable claw 115c is engaged in the surface of the ultrasonic acoustic coupler, thereby fixing the ultrasonic acoustic coupler. On the other hand, when the ultrasonic acoustic coupler is to be detached, the movable claw 115c is pivoted into a position shown in part (B) of FIG. 18. Then, the movable claw 115c is disengaged from the ultrasonic acoustic coupler, whereby the ultrasonic acoustic coupler is detached therefrom.

Figure 19:
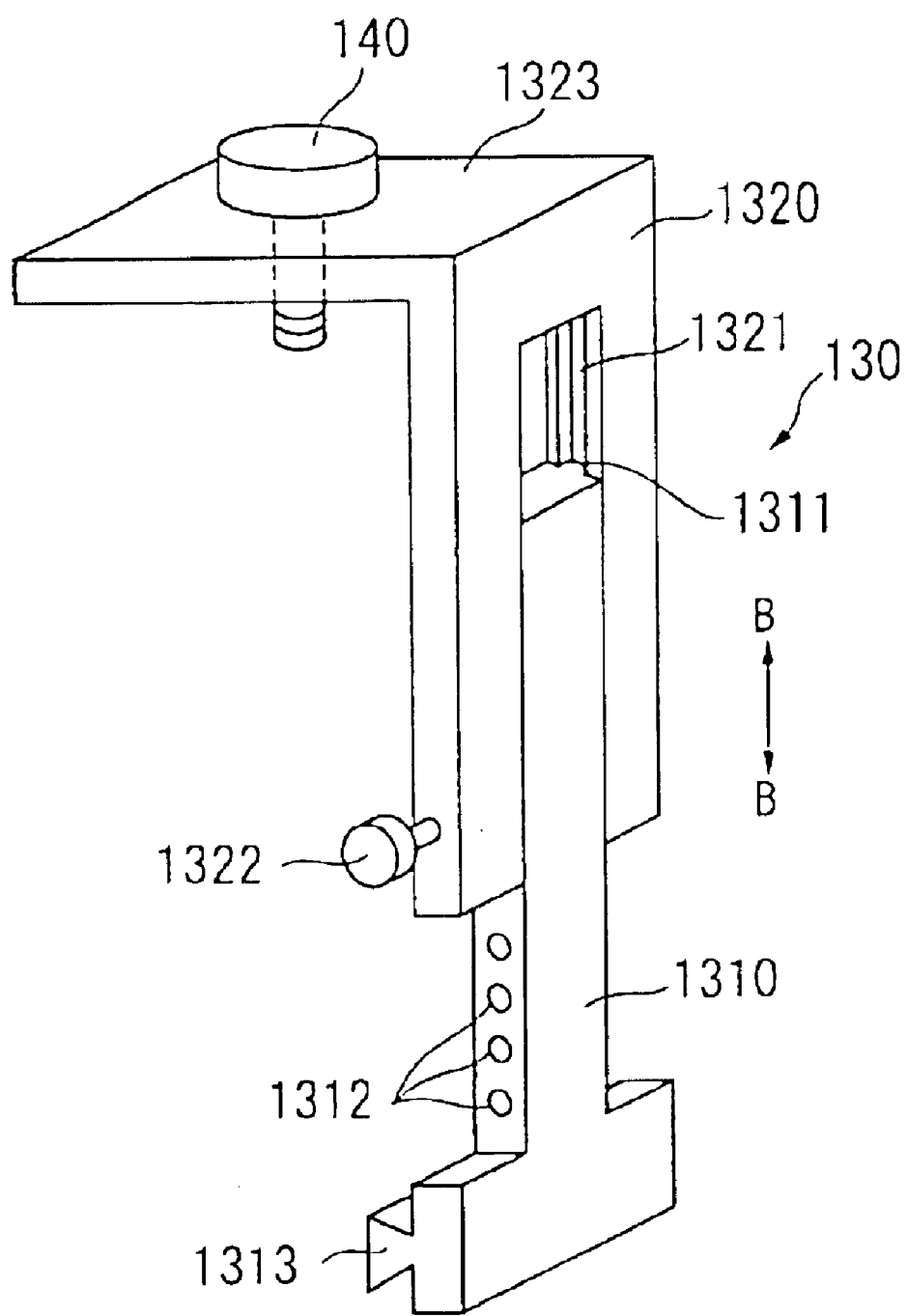
FIG. 19 shows a variation of a probe unit holder.

FIG. 19 shows a variation of the probe unit holder.

The probe unit holder 130 of the measuring section 100 shown in part (A) of FIG. 16 is to support the ultrasonic probe 11 at a fixed level. However, if the probe unit holder 130 shown in FIG. 19 is used, the level of the ultrasonic probe 11 supported by the probe unit holder 130 can be adjusted.

The probe unit holder 130 shown in FIG. 19 has a lower member 1310 and an upper member 1320. The upper member 1320 has a guide groove 1321 extending longitudinally formed therein, and the lower member 1310 has a protrusion 1311 which is to be fitted into the guide groove 1321 formed therein. The upper member 1320 is guided by engagement of the guide groove 1321 and the protrusion 1311 and thus can move vertically (in the direction indicated by arrow B—B in the drawing).

The upper member 1320 is provided with a stopper 1322 which is detachably inserted into a stopper through hole (not shown) formed in a side wall of the upper member. On the other hand, in a side wall of the lower member 1310, there are formed and longitudinally arranged plural stopper receiving holes 1312 into which the tip of the stopper 1322 is inserted.

Therefore, the upper member 1320 is adjusted to a level in a state where the stopper 1322 is detached, and then the stopper 1322 is inserted through the stopper through hole in the upper member 1320 into any one of the plural stopper receiving holes 1312, whereby the upper member 1320 is fixed at the level. A top plate 1323 of the upper member 1320 is provided with an external thread 140 with a knob, which is also shown in FIG. 16, and the ultrasonic probe is fixed to the bottom surface of the top plate 1323.

When the level of the upper member 1320 is adjusted, the level of the ultrasonic probe fixed to the top plate 1323 of the upper member 1320 is also adjusted accordingly.

In addition, on the lower member 1310 an engagement protrusion 1313 is formed which is slidably engaged with the engagement recess 121 formed in the mount 120 of the measuring section 100 shown in part (A) of FIG. 16, so that the probe unit holder 130 shown in FIG. 19 is also supported by the mount 120 shown in part (A) of FIG. 16 and can slide in the direction indicated by arrow A—A.

Figure 20:
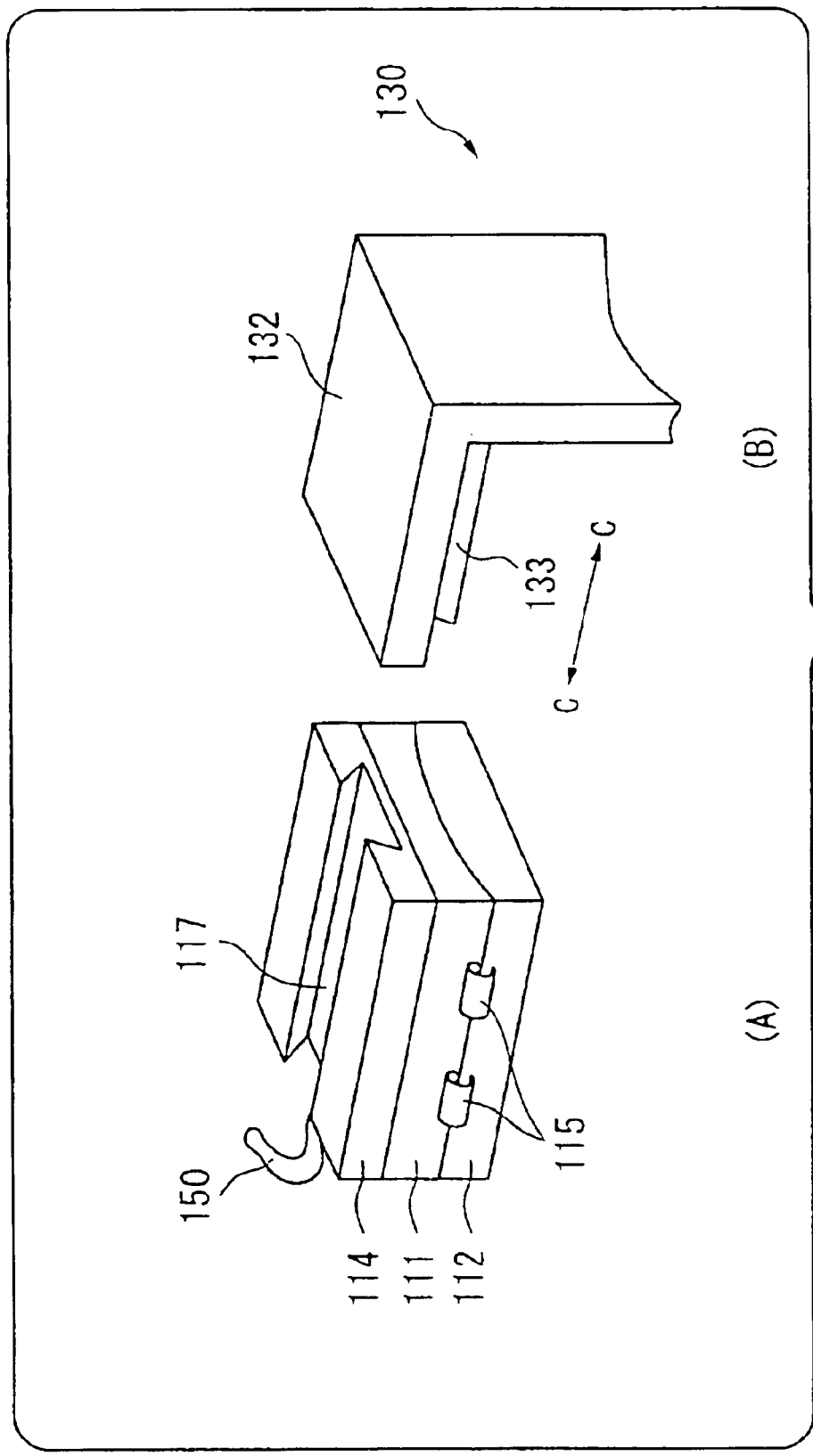
FIG. 20 shows variations of the ultrasonic probe (A) and a top plate of the probe unit holder (B)

FIG. 20 shows variations of the ultrasonic probe in part (A) and the top plate of the probe unit holder in part (B).

The ultrasonic probe shown in FIG. 17 has the internal thread hole 116 for attachment to the top plate of the probe unit holder formed in the base 114. However, the ultrasonic probe shown in part (A) of FIG. 20 has a sliding groove 117 rather than the internal thread hole. And so as to conform to this, on the top plate 132 of the probe unit holder 130 shown in part (B) of FIG. 20, a fitting protrusion 133 is formed which is fitted into the sliding groove 117 of the ultrasonic probe to hold the ultrasonic probe slidably along the length of the slide groove 117 (in the direction indicated by arrow C—C).

In this way, the probe unit holder 130 of the measuring section 100 shown in part (A) of FIG. 16 is allowed to move not only in the direction of arrow A—A shown in part (A) of FIG. 16 but also in the height direction (in the direction of arrow B—B) as shown in FIG. 19 as well as in the direction of arrow C—C as shown in FIG. 20. Thus, the ultrasonic probe 11 can be adjusted in position or moved three-dimensionally.

Figure 21:
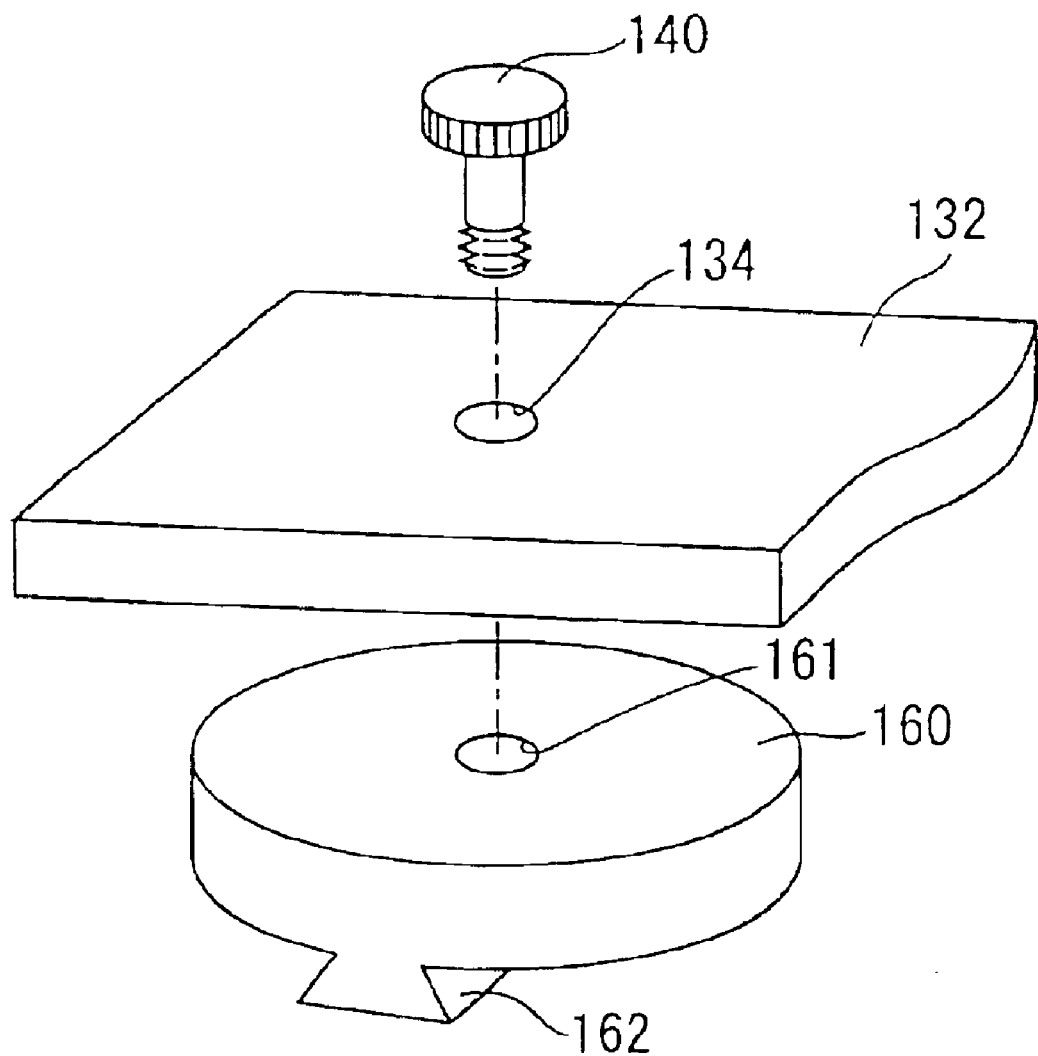
FIG. 21 shows another attachment mechanism for attaching the ultrasonic probe to the top plate of the probe unit holder.

FIG. 21 shows another attachment mechanism for attaching the ultrasonic probe to the top plate of the probe unit holder.

In the top plate 132 of the probe unit holder shown in FIG. 21, a hole 134 through which the external thread 140 with a knob is to pass is formed, and the external thread 140 with a knob is inserted into the hole 134. The arrangement so far is the same as in the example shown in FIG. 16. However, unlike the example shown in FIG. 16 in which the ultrasonic probe 11 is directly attached to the top plate 132 by the external thread 140, in the example shown in FIG. 21, the external thread 140 attaches a rotatable base 160 to the top plate 132. In the top surface of the rotatable base 160, an internal thread hole 161 to be engaged with the external thread 140 is formed. Screwing the tip of the external thread 140 into the internal thread hole 161 through the hole 134 in the top plate 132 can attach the rotatable base 160 to the top plate 132. Although the rotatable base 160 is attached to the top plate 132, it can be rotated about the internal thread hole 161 by a rotational force.

On the bottom of the rotatable base 160, a fitting protrusion 162 is formed which is fitted into the sliding groove 117 in the base 114 of the ultrasonic probe configured as shown in part (A) of FIG. 20 to support the ultrasonic probe slidably along the length of the sliding groove 117 (in the direction of arrow C—C in part (A) of FIG. 20).

With the attachment mechanism shown in FIG. 21, the ultrasonic probe configured as shown in part (A) of FIG. 20 can be rotatably and slidably attached to the top plate 132 of the probe unit holder.

Rotatably attaching the ultrasonic probe allows one blood vessel to be observed in both the longitudinal section shown in part (A) of FIG. 9 and the cross section shown in part (B) of FIG. 9.

Figure 22:
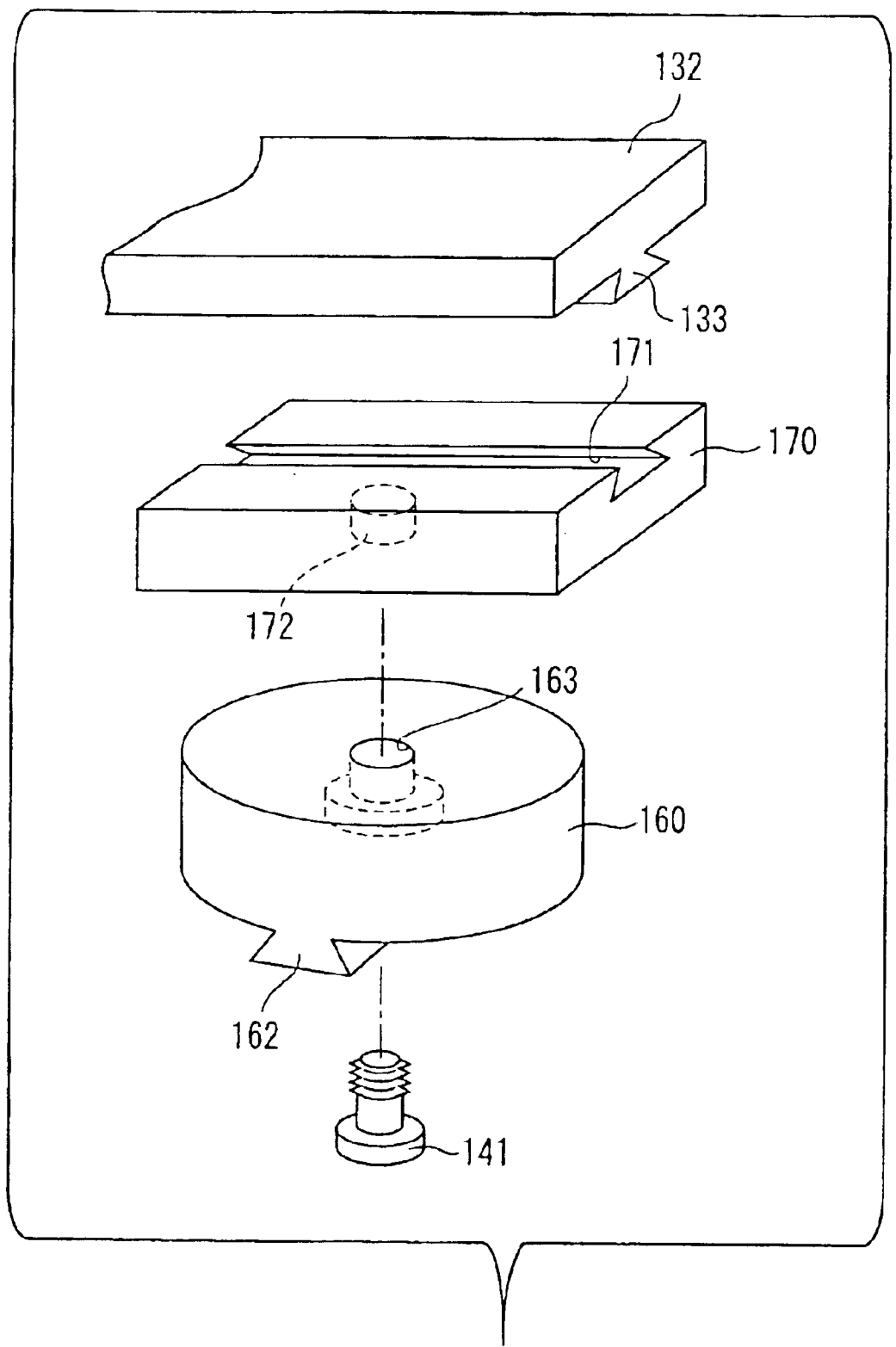
FIG. 22 shows another attachment mechanism for attaching the ultrasonic probe to the top plate of the probe unit holder.

FIG. 22 shows another attachment mechanism for attaching the ultrasonic probe to the top plate of the probe unit holder.

As with the top plate 132 shown in part (B) of FIG. 20, a fitting protrusion 133 is formed on the bottom of the top plate 132 of the probe unit holder shown in FIG. 22. Fitting the fitting protrusion 133 into a sliding groove 171 formed in the top surface of a slidable base 170 can slidably attach the slidable base 170 to the top plate 132 of the probe unit holder.

In addition, on the bottom of the slidable base 170, an internal thread hole 172 is formed into which an external thread 141 with a knob is screwed.

The rotatable base 160 has a through hole 163 formed at the center thereof. The tip of the external thread 141 is screwed into the internal thread hole 172 in the slidable base 170 through the through hole 163, and the rotatable base 160 is attached to the slidable base 170 by the external thread 141 with a knob. Here, the through hole 163 in the rotatable base 160 is shaped so as to accommodate the entire external thread 141 with a knob including the knob part. Thus, when the rotatable base 160 is attached to the slidable base 170, the entire external thread 141 with a knob including the knob part is accommodated in the through hole 163. The rotatable base 160 rotates about the through hole 163 if a rotational force is applied thereto when it is attached to the slidable base 170. On the bottom surface of the rotatable base 160, a fitting protrusion 162 is formed which is fitted into the sliding groove 117 in the ultrasonic probe base 114 configured as shown in part (A) of FIG. 20.

Therefore, with the attachment mechanism shown in FIG. 22, the slidable base 170 can slide to any location relative to the top plate 132 of the probe unit holder, the rotatable base 160 can be rotated about the internal thread hole 172 in the slidable base 170, and furthermore, the ultrasonic probe shown in part (A) of FIG. 20 can slide relative to the rotatable base 160. Thus, the ultrasonic probe can have a higher degree of flexibility in adjustment of position and rotation angle.

Figure 23:
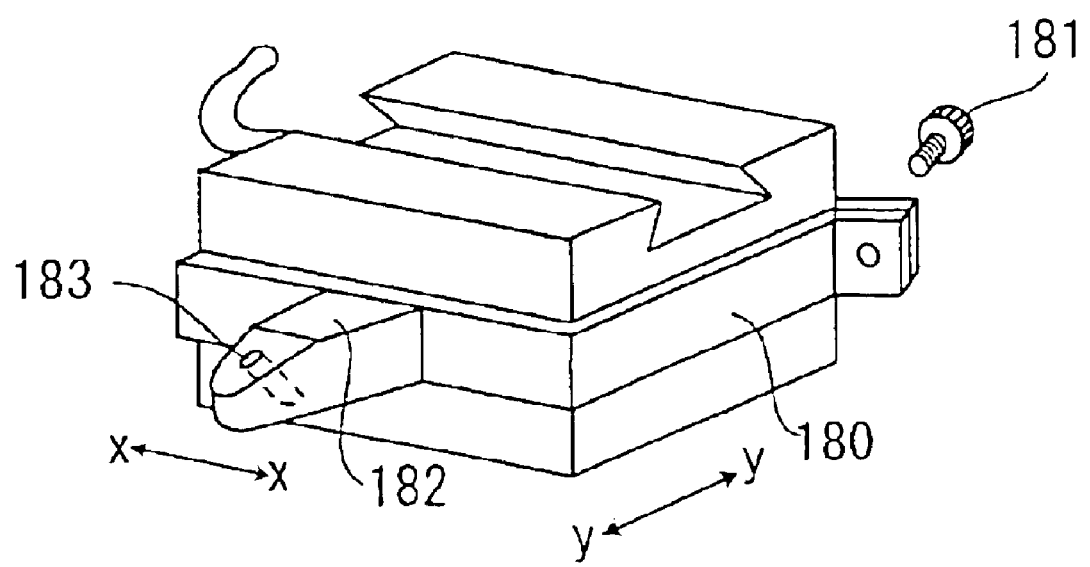
FIG. 23 is a perspective view of the ultrasonic probe shown in part (A) of FIG. 20 with a puncture guide member attached thereto.

FIG. 23 is a perspective view of the ultrasonic probe shown in part (A) of FIG. 20 with a puncture guide member attached thereto.

In this drawing, a puncture guide member 180 surrounding the side wall of the ultrasonic probe shown in part (A) of FIG. 20 is fixed to the ultrasonic probe by a screw 181.

The puncture guide member 180 has a puncture guide protrusion 182, and a needle insertion hole 183 is formed diagonally in the puncture guide protrusion so as to guide the tip of a needle inserted thereto to a site directly below the ultrasonic probe.

FIG. 23 shows an example of the puncture guide member, in which the puncture guide member is of a type which allows puncture from the direction crossing the arrangement direction of the ultrasonic transducers (x—x direction in FIGS. 11 and 23). Besides, the puncture guide member may be of a type which allows puncture from the direction crossing the lateral direction of the ultrasonic transducers (y—y direction in FIGS. 11 and 23).

Figure 24:
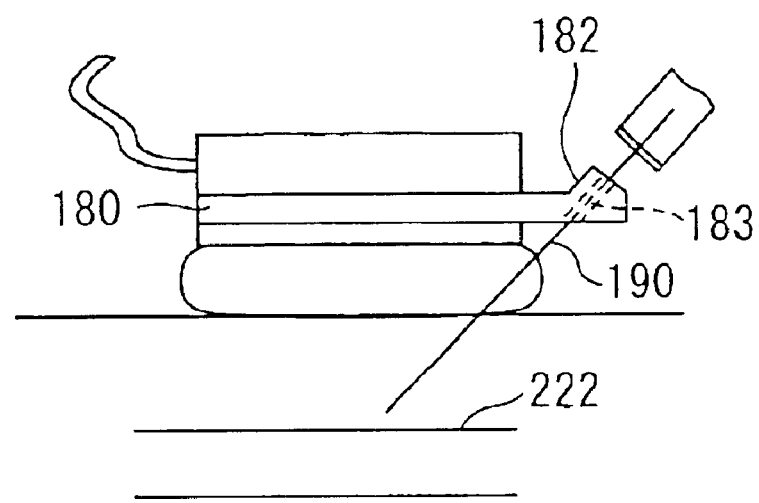
FIG. 24 shows a first implementation of puncture difficulty investigation and puncture using an ultrasonic probe with a puncture guide member attached thereto.

FIG. 24 shows a first implementation of puncture difficulty investigation and puncture using an ultrasonic probe with a puncture guide member attached thereto.

In this case, a blood vessel is scanned with an ultrasound so that the resulting B-mode image exhibits a longitudinal section of the blood vessel.

An injection needle 190 is inserted into the needle insertion hole 183 in the puncture guide member 180. As the injection needle 190 is further inserted through the needle insertion hole 183, the front end of the injector (rear part of the injection needle) abuts against the puncture guide protrusion 182, and therefore, further puncture is impossible. The position of the tip of the injection needle 190 at that time is the puncture destination point.

Figure 25:
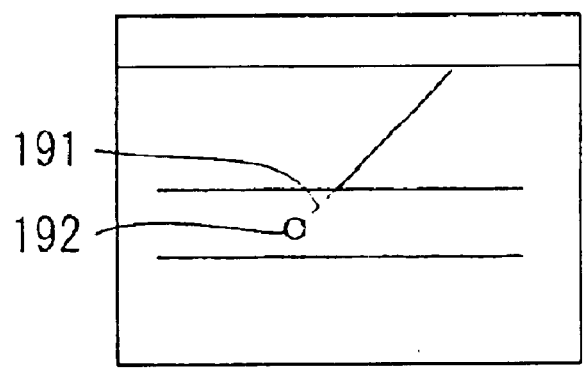
FIG. 25 is a schematic view of a B-mode image obtained in the measurement shown in FIG. 24.

FIG. 25 is a schematic view of a B-mode image obtained in the measurement shown in FIG. 24.

In the arrangement shown in FIG. 8, when the manipulation section 27 is manipulated to input information such as the fact that the puncture guide member is attached to the ultrasonic probe or the type of the puncture guide member, the graphic generating section 28 generates a mark 191 showing the path of the puncturing needle and a mark 192 showing the destination point of the tip of the needle, which are displayed by being superposed on the B-mode image before the puncture is started.

Thus, a person who perform puncture, such as a doctor, can check the path of the needle during puncture and the destination point of the tip of the needle before performing puncture, and therefore, puncture can be attained without fail.

Figure 26:
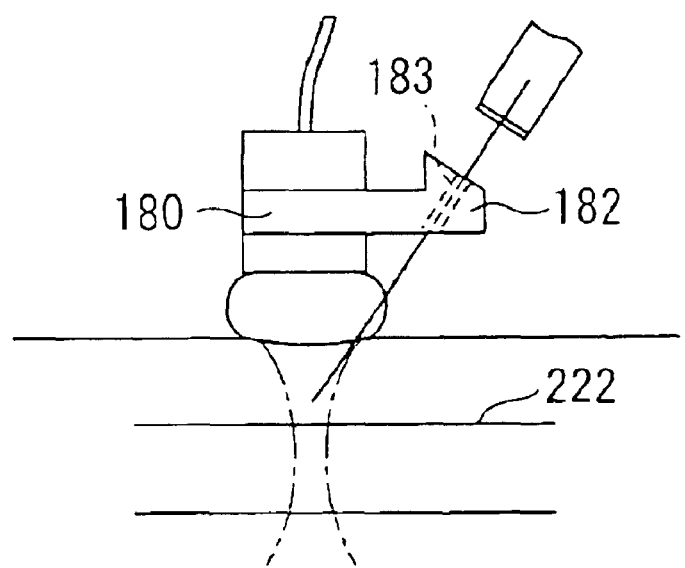
FIG. 26 shows a second implementation of puncture difficulty investigation and puncture using an ultrasonic probe with a puncture guide member attached thereto.

FIG. 26 shows a second implementation of puncture difficulty investigation and puncture using an ultrasonic probe with a puncture guide member attached thereto.

In FIG. 24, the ultrasonic probe is oriented in such a direction that the blood vessel 222 is scanned with the ultrasound along the sheet surface of FIG. 24 to produce a B-mode image exhibiting a longitudinal section of the blood vessel 222. However, in FIG. 26, the orientation of the ultrasonic probe is changed by 90 degrees, and the ultrasonic probe is oriented in such a direction that the blood vessel 222 is scanned with the ultrasound in a direction perpendicular to the sheet surface of FIG. 26 to produce a B-mode image exhibiting a cross section of the blood vessel 222. In addition, in FIG. 26, the puncture guide protrusion 182 of the puncture guide member 180 is also oriented with respect to the ultrasonic probe in a direction different by 90 degrees from that of the puncture guide member shown in FIG. 24.

Figure 27:
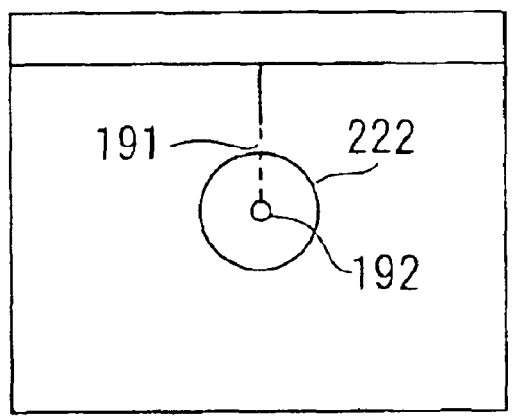
FIG. 27 is a schematic view of a B-mode image obtained in the measurement shown in FIG. 26.

FIG. 27 is a schematic view of a B-mode image obtained in the measurement shown in FIG. 26.

This drawing shows a cross section of the blood vessel 222, and the mark 191 showing the path of the needle approaching the blood vessel 222 and the mark 192 showing the destination point of the tip of the needle are displayed by being superposed on this B-mode image.

As described above, according to the present invention, the difficulty of puncture can be readily evaluated, and thus puncture and treatment can be performed without fail.

What is claimed is:

1. A puncture difficulty evaluating device, comprising:
an ultrasonic transmitting section that irradiates a measurement point of a specimen with an ultrasonic pulse;
an ultrasound receiver section that receives the ultrasound backscattered at the measurement point and determines an integral of the power of the ultrasound over a predetermined angle range; and
a parameter generating section that generates a parameter indicating the difficulty of puncture in the measurement point based on the integral determined in the ultrasonic receiver section.

2. The puncture difficulty evaluating device according to claim 1, wherein the ultrasonic receiver section determines a first integral of the power of the ultrasound backscattered at the measurement point over a first predetermined angle range and a second integral of the power of the ultrasound backscattered at the measurement point over a second predetermined angle range that is different from the first angle range, and
the parameter generating section generates the parameter based on both the first integral and the second integral determined in the ultrasonic receiver section.

3. The puncture difficulty evaluating device according to claim 2, wherein the parameter generating section generates the parameter by determining the ratio between the first integral and the second integral.

4. The puncture difficulty evaluating device according to claim 2, wherein the parameter generating section generates the parameter by determining the difference between the first integral and the second integral.

5. The puncture difficulty evaluating device according to claim 2, wherein the parameter generating section generates the parameter by determining the ratio between the difference between the first integral and the second integral and the difference between the first angle and the second angle.

6. The puncture difficulty evaluating device according to claim 1, further comprising a puncture difficulty determining section that determines the difficulty of puncture at the measurement point by comparing the parameter determined in the parameter generating section with a predetermined comparative evaluation reference value.

7. The puncture difficulty evaluating device according to claim 1, wherein the ultrasonic transmitting section irradiates each measurement point with an ultrasonic pulse emitted from one ultrasonic transducer from a position distant from the measurement point by such an amount that the measurement point lies in a far sound field.

8. The puncture difficulty evaluating device according to claim 1, further comprising plural ultrasonic transducers arranged, wherein the ultrasonic transmitting section emits, from the plural ultrasonic transducers, ultrasonic pulses whose phases are controlled for the ultrasonic pulses to be focused on a predetermined measurement point.

9. The puncture difficulty evaluating device according to claim 1, wherein the ultrasonic transmitting section sequentially irradiates plural measurement points with ultrasonic pulses,
the ultrasonic receiver section sequentially receives ultrasounds backscattered at the plural measurement points and sequentially determines integrals for the respective measurement points, and
the parameter generating section generates a parameter indicating the difficulty of puncture in each of the plural measurement points.

10. The puncture difficulty evaluating device according to claim 1, further comprising:
a B-mode image generating section that transmits an ultrasonic pulse to the specimen, receives an ultrasound backscattered in the specimen and generates a B-mode image; and an image display section that displays the B-mode image and an indication of the difficulty of puncture at the measurement point on the B-mode image, the indication being generated based on the parameter generated in said parameter generating section.

11. The puncture difficulty evaluating device according to claim 1, further comprising an ultrasonic probe for transmitting and receiving an ultrasound, wherein the ultrasonic transmitting section irradiates the measurement point with an ultrasonic pulse from the ultrasonic probe, and the ultrasonic receiver section receives the backscattered ultrasound at the ultrasonic probe.

12. The puncture difficulty evaluating device according to claim 11, further comprising:
   a holding mechanism for holding the ultrasonic probe; and
   a guide mechanism that fixes the specimen and guides the movement of the holding mechanism, thereby guiding the movement of the ultrasonic probe supported by the holding mechanism along the specimen.

13. The puncture difficulty evaluating device according to claim 12, wherein the holding mechanism supports the ultrasonic probe in such a manner that the position of the ultrasonic probe can be adjusted in a direction toward or away from the specimen.

14. The puncture difficulty evaluating device according to claim 12, wherein the holding mechanism supports the ultrasonic probe slidably in a direction crossing the direction in which the holding mechanism guided by the guide mechanism moves.

15. The puncture difficulty evaluating device according to claim 12, further comprising a puncture guide mechanism that guides puncture into the specimen fixed to the guide mechanism.

16. The puncture difficulty evaluating device according to claim 15, further comprising:
   a B-mode image generating section that transmits an ultrasonic pulse to the specimen fixed to the guide mechanism, receives an ultrasound backscattered in the specimen and generates a B-mode image; and
   an image display section that displays the B-mode image generated in the B-mode image generating section and displays, on the B-mode image, a destination point which is reached by the tip of a needle guided by the puncture guide mechanism to a puncture terminal point in the specimen.

17. The puncture difficulty evaluating device according to claim 11, wherein the ultrasonic probe comprises:
   plural ultrasonic transducers having front surfaces facing the specimen concaved along a first direction and arranged in a second direction crossing the first direction;
   a flexible acoustic coupler removably mounted on the front surfaces of the plural ultrasonic transducers; and
   an acoustic coupler attachment mechanism that removably attaches the flexible acoustic coupler to the front surfaces of the plural ultrasonic transducers.

* * * * *